(12) United States Patent
Engel et al.

(10) Patent No.: US 11,136,376 B2
(45) Date of Patent: Oct. 5, 2021

(54) RECOMBINANT IMMUNOGLOBULIN HEAVY CHAINS COMPRISING A SORTASE CONJUGATION LOOP AND CONJUGATES THEREOF

(71) Applicant: Roche Diagnostics Operations, Inc., Indianapolis, IN (US)

(72) Inventors: Alfred Engel, Weilheim (DE); Pavel Kubalec, Feldafing (DE); Alfons Nichtl, Hohenpeissenberg (DE); Tobias Oelschlaegel, Munich (DE); Rainer Schlecht, Frankfurt am Main (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 263 days.

(21) Appl. No.: 15/934,055

(22) Filed: Mar. 23, 2018

(65) Prior Publication Data
US 2021/0009660 A1  Jan. 14, 2021

Related U.S. Application Data

(63) Continuation of application No. PCT/EP2016/072529, filed on Sep. 22, 2016.

(30) Foreign Application Priority Data

Sep. 25, 2015 (EP) .................................... 15186821

(51) Int. Cl.
*C07K 16/00* (2006.01)

(52) U.S. Cl.
CPC .......... *C07K 16/00* (2013.01); *C07K 2317/51* (2013.01); *C07K 2317/522* (2013.01); *C07K 2317/524* (2013.01); *C07K 2317/526* (2013.01); *C07K 2317/53* (2013.01)

(58) Field of Classification Search
CPC combination set(s) only.
See application file for complete search history.

(56) References Cited

U.S. PATENT DOCUMENTS

| | | | |
|---|---|---|---|
| 4,275,149 A | 6/1981 | Litman et al. | |
| 4,318,980 A | 3/1982 | Boguslaski et al. | |
| 4,737,456 A | 4/1988 | Weng et al. | |
| 5,316,757 A | 5/1994 | Sherry et al. | |
| 5,342,606 A | 8/1994 | Sherry et al. | |
| 5,385,893 A | 1/1995 | Kiefer | |
| 5,428,139 A | 6/1995 | Kiefer et al. | |
| 5,428,155 A | 6/1995 | Sherry et al. | |
| 5,462,725 A | 10/1995 | Kiefer et al. | |
| 5,480,990 A | 1/1996 | Kiefer et al. | |
| 5,648,237 A | 7/1997 | Carter | |
| 5,739,294 A | 4/1998 | Kiefer et al. | |
| 5,750,660 A | 5/1998 | Kiefer et al. | |
| 5,789,199 A | 8/1998 | Joly et al. | |
| 5,834,456 A | 11/1998 | Kiefer et al. | |
| 5,840,523 A | 11/1998 | Simmons et al. | |
| 5,959,177 A | 9/1999 | Hein et al. | |
| 6,040,498 A | 3/2000 | Stomp et al. | |
| 6,417,429 B1 | 7/2002 | Hein et al. | |
| 6,420,548 B1 | 7/2002 | Vezina et al. | |
| 6,528,624 B1 | 3/2003 | Idusogie et al. | |
| 7,125,978 B1 | 10/2006 | Vezina et al. | |
| 2011/0111856 A1 | 5/2011 | White et al. | |
| 2021/0009660 A1 | 1/2021 | Engel et al. | |

FOREIGN PATENT DOCUMENTS

| | | |
|---|---|---|
| DE | 19637718 A1 | 10/1997 |
| JP | 2018515618 A | 6/2018 |
| WO | 1993/021232 A1 | 10/1993 |
| WO | 1994/011026 A2 | 5/1994 |
| WO | 2012/028697 A1 | 3/2012 |
| WO | 2012/107419 A1 | 8/2012 |
| WO | 2013/003555 A1 | 1/2013 |
| WO | 2014/001324 A1 | 1/2014 |
| WO | 2014/001325 A1 | 1/2014 |
| WO | WO 2014/001325 * | 1/2014 |
| WO | 2014/041072 A1 | 3/2014 |
| WO | 2013/155526 A2 | 10/2018 |

OTHER PUBLICATIONS

Beerli, Roger R. et al., Sortase Enzyme-Mediated Generation of Site-Specifically Conjugated Antibody Drug Conjugates with High In Vitro and In Vivo Potency, PLoS One, 2015, e0131177, 17 pp., vol. 10, No. 7.
Blend, Michael J. et al., Labeling anti-HER2/neu Monoclonal Antibodies with 111In and 90Y Using a Bifunctional DTPA Chelating Agent, Cancer Biotherapy & Radiopharmaceuticals, 2003, pp. 355-363, vol. 18, No. 3.
Briggs, Mark S. J. et al., Synthesis of functionalised fluorescent dyes and their coupling to amines and amino acids, Journal of the American Chemical Society, Perkin Trans. 1, 1997, pp. 1051-1058.
Camera, L. et al., Evaluation of a new DTPA-derivative chelator: comparative biodistribution and imaging studies of 111In-labeled B3 monoclonal antibody in athymic mice bearing human epidermoid carcinoma xenografts, Nuclear Medicine and Biology, 1994, pp. 955-962, Abstract only, vol. 21.
Camera, Luigi et al., Comparative biodistribution of indium- and yttrium-labeled B3 monoclonal antibody conjugated to either 2-(p-SCN-Bz)-6-methyl-DTPA (1B4M-DTPA) or 2-(p-SCN-Bz)-1,4,7,10-tetraazacyclododecane tetraacetic acid (2B-DOTA), European Journal of Nuclear Medicine, 1994, pp. 640-646, vol. 21.
Charlton, Keith A., Expression and Isolation of Recombinant Antibody Fragments in *E. coli*, Methods in Molecular Biology, 2003, pp. 245-254, vol. 248.
Chen, Xiaoyuan et al., MicroPET and Autoradiographic Imaging of Breast Cancer αv-Integrin Expression Using 18F- and 64Cu-Labeled RGD Peptide, Bioconjugate Chemistry, 2004, pp. 41-49, vol. 15, No. 1.

(Continued)

*Primary Examiner* — Laura B Goddard
(74) *Attorney, Agent, or Firm* — Stinson LLP

(57) ABSTRACT

The disclosure describes a recombinant immunoglobulin heavy chain comprising a sortase conjugation loop, methods for conjugating and/or labeling such recombinant immunoglobulin heavy chains by use of the enzyme sortase and to the conjugates/labeled products obtained via the method.

13 Claims, 7 Drawing Sheets
Specification includes a Sequence Listing.

(56) References Cited

OTHER PUBLICATIONS

Clancy, Kathleen W. et al., Sortase Transpeptidases: Insights Into Mechanism, Substrate Specificity, and Inhibition, Peptide Science, 2010, pp. 385-396, vol. 94, No. 4.
Denardo, Gerald L. et al., Comparison of 1,4,7,10-Tetraazacyclododecane-N,N',N",N"'-tetraacetic acid (DOTA)-Peptide-ChL6, a Novel Immunoconjugate with Catabolizable Linker, to 2-Iminothiolane-2[p-(Bromoacetamido)benzyl]-DOTA-ChL6 in Breast Cancer Xenografts, Clinical Cancer Research, 1998, pp. 2483-2490, vol. 4.
Dodeigne, C. et al., Chemiluminescence as diagnostic tool. A review, Talanta, 2000, pp. 415-439, vol. 51.
Ellman, Jon et al., Biosynthetic Method for Introducing Unnatural Amino Acids Site-Specifically into Proteins, Methods in Enzymology, 1991, pp. 301-336, vol. 202.
Fraker, Pamela J. and Speck, John C. Jr., Protein and Cell Membrane Iodinations with a Sparingly Soluble Chloroamide, 1,3,4,6-Tetrachloro-3a,6a-Diphenylglycoluril, Biochemical and Biophysical Research Communications, 1978, pp. 849-857, vol. 80, No. 4.
Gerngross, Tillman U., Advances in the production of human therapeutic proteins in yeasts and filamentous fungi, Nature Biotechnology, 2004, pp. 1409-1414, vol. 22, No. 11.
Guimaraes, Carla P. et al., Site-specific C-terminal and internal loop labeling of proteins using sortase-mediated reactions, Nature Protocols, 2013, pp. 1787-1799, vol. 8, No. 9.
Hnatowich, D.J. et al., The Preparation of DTPA-Coupled Antibodies Radiolabeled with Metallic Radionuclides: an Improved Method, Journal of Immunological Methods, 1983, pp. 147-157, vol. 65.
Ilangovan, Udayar et al., Structure of sortase, the transpeptidase that anchors proteins to the cell wall of Staphylococcus aureas, Proceedings of the National Academy of Sciences USA, 2001, pp. 6056-6061, vol. 98.
International Search Report dated Nov. 11, 2016, in Application No. PCT/EP2016/072529, 7 pps.
Izard, M. E. et al., An Improved Method for Labeling Monoclonal Antibodies with Samarium-153: Use of the Bifunctional Chelate 2-(p-Isothiocyanatobenzyl)-6-methyldiethylenetriaminepentaacetic Acid, Bioconjugate Chemistry, 1992, pp. 346-350, vol. 3.
Kabat et al., Sequences of Proteins of Immunological Interest, U. S. Department of Health and Human Services, 1991, pp. 647-723, vol. 1, Fifth Edition, Public Health Service, National Institutes of Health, Bethesda, Maryland.
Kobayashi, Hisataka et al., Evaluation of the in Vivo Biodistribution of Indium-111 and Yttrium-88 Labeled Dendrimer-1B4M-DTPA and Its Conjugation with Anti-Tac Monoclonal Antibody, Bioconjugate Chemistry, 1999, pp. 103-111, vol. 10.
Kobayashi, Hisataka et al., Evaluation of the in Vivo Biodistribution of Yttrium-Labeled Isomers of CHX-DTPA-Conjugated Monoclonal Antibodies, Journal of Nuclear Medicine, 1998, pp. 829-836, vol. 39.
Kukis, David L. et al., Optimized Conditions for Chelation of Yttrium-90-DOTA Immunoconjugates, Journal of Nuclear Medicine, 1998, pp. 2105-2110, vol. 39.
Lee, Fook-Thean et al., Specific Localization, Gamma Camera Imaging, and Intracellular Trafficking of Radiolabelled Chimeric Anti-GD3 Ganglioside Monoclonal Antibody KM871 in SK-MEL-28 Melanoma Xenografts, Cancer Research, 2001, pp. 4474-4482, vol. 61.
Levary, David A. et al., Protein-Protein Fusion Catalyzed by Sortase A, PLoS One, 2011, e18342, 6 pp., vol. 6, No. 4.
Li, Huijuan et al., Optimization of humanized IgGs in glycoengineered Pichia pastoris, Nature Biotechnology, 2006, pp. 210-215, vol. 24, No. 2.
Madej, Mariusz P. et al., Engineering of an Anti-Epidermal Growth Factor Receptor Antibody to Single Chain Format and Labeling by Sortase A-Mediated Protein Ligation, Biotechnology and Bioengineering, 2012, pp. 1461-1470, vol. 109.
Mardirossian, G. et al., The stability in liver homogenates of indium-111 and yttrium-90 attached to antibody via two popular chelators, Nuclear Medicine and Biology, 1993, pp. 65-74, vol. 20, No. 1.
Marvin, Jonathan S. and Zhu, Zhenping, Recombinant approaches to IgG-like bispecific antibodies, Acta Pharmacologica Sinica, 2005, pp. 649-658, vol. 26, No. 6.
Meares, C F. et al., Macrocyclic chelates of radiometals for diagnosis and therapy, British Journal of Cancer, 1990, pp. 21-26, vol. 62, Supp X.
Meares, Claude F. et al., Conjugation of Antibodies with Bifunctional Chelating Agents: Isothiocyanate and Bromoacetamide Reagents, Methods of Analysis, and Subsequent Addition of Metal Ions, Analytical Biochemistry, 1984, pp. 68-78, vol. 142.
Meissner, Petra et al., Transient Gene Expression: Recombinant Protein Production with Suspension-Adapted HEK293-EBNA Cells, Biotechnology and Bioengineering, 2001, pp. 197-203, vol. 75.
Miederer, Matthias et al., Pharmacokinetics, Dosimetry, and Toxicity of the Targetable Atomic Generator, 225Ac-HuM195, in Nonhuman Primates, Journal of Nuclear Medicine, 2004, pp. 129-137, vol. 45.
Mirzadeh, Saed et al., Radiometal Labeling of Immunoproteins: Covalent Linkage of 2-(4-Isothiocyanatobenzyl) diethylenetriaminepentaacetic Acid Ligands to Immunoglobulin, Bioconjugate Chemistry, 1990, pp. 59-65, vol. 1.
Mitchell, Paul et al., Targeting Primary Human Ph+ B-Cell Precursor Leukemia-Engrafted SCID Mice Using Radiolabeled Anti-CD19 Monoclonal Antibodies, Journal of Nuclear Medicine, 2003, pp. 1105-1112, vol. 44.
Mikula, Tuomo K. et al., A Rapid, Single Vessel Method for Preparation of Clinical Grade Ligand Conjugated Monoclonal Antibodies, Nuclear Medicine and Biology, 1995, pp. 387-390, vol. 22, No. 3.
Nikula, Tuomo K. et al., Alpha-Emitting Bismuth Cyclohexylbenzyl DTPA Constructs of Recombinant Humanized Anti-CD33 Antibodies: Pharmacokinetics, Bioactivity, Toxicity and Chemistry, Journal of Nuclear Medicine, 1999, pp. 166-176, vol. 40.
Noren, Christopher J. et al., A General Method for Site-Specific Incorporation of Unnatural Amino Acids into Proteins, Science, 1989, pp. 182-188, vol. 244.
Popp, Maximilian Wei-Lin and Ploegh, Hiddle L., Making and Breaking Peptide Bonds: Protein Engineering Using Sortase, Angew. Chem. Int. Ed., 2011, pp. 5024-5032, vol. 50.
Rashidian, Mohammad et al., Enzymatic Labeling of Proteins: Techniques and Approaches, Bioconjugate Chemistry, 2013, pp. 1277-1294, vol. 24.
Roselli, Mario et al., In Vivo Comparison of CHX-DTPA Ligand Isomers in Athymic Mice Bearing Carcinoma Xernografts, Cancer Biotherapy & Radiopharmaceuticals, 1999, pp. 209-220, vol. 14, No. 3.
Roux, Kenneth H. et al., Comparisons of the Ability of Human IgG3 Hinge Mutants, IgM, IgE, and IgA2, to Form Small Immune Complexes: A Role for Flexibility and Geometry, Journal of Immunology, 1998, pp. 4083-4090, vol. 161.
Ruegg, Curtis L. et al., Improved in Vivo Stability and Tumor Targeting of Bismuth-labeled Antibody, Cancer Research, 1990, pp. 4221-4226, vol. 50.
Singh, Rajeeva and Maloney, Erin K., Labeling of Antibodies by in Siitu Modification of Thiol Groups Generated from Selenol-Catalyzed Reduction of Native Disulfide Bonds, Analytical Biochemistry, 2002, pp. 147-156, vol. 304.
Ta, H.T. et al., Enzymatic Single-Chain Antibody Tagging, Circulation Research, 2011, pp. 365-373, vol. 109.
Tinianow, Jeff N. et al., Site-specifically 89Zr-labeled monoclonal antibodies for ImmunoPET, Nuclear Medicine and Biology, 2010, pp. 289-297, vol. 37.
Ton-That, Hung et al., Purification and characterization of sortase, the transpeptidase that cleaves surface proteins of Staphylococcus aureus at the LPXTG motif, PNAS, 1999, pp. 12424-12429, vol. 96, No. 22.
Tsukiji, Shinya and Nagamune, Teruyuki, Sortase-Mediated Ligation: A Gift from Gram-Positive Bacteria to Protein Engineering, ChemBioChem, 2009, pp. 787-798, vol. 10.

(56) References Cited

OTHER PUBLICATIONS

Urlaub, Gail and Chasin, Lawrence A., Isolation of Chinese hamster cell mutants deficient in dihydrofolate reductase activity, Proceedings of the National Academy of Sciences USA, 1980, pp. 4216-4220, vol. 77, No. 7.

Verel, Iris et al., Quantitative 89Zr Immuno-PET for In Vivo Scouting of 90Y-Labeled Monoclonal Antibodies in Xenograft-Bearing Nude Mice, Journal of Nuclear Medicine, 2003, pp. 1663-1670, vol. 44.

Yazaki, Paul J. and Wu, Anna M., Expression of Recombinant Antibodies in Mammalian Cell Lines, Methods in Molecular Biology, 2004, pp. 255-268, vol. 248.

Zola, H., Using Monoclonal Antibodies: Soluble Antigens, Monoclonal Antibodies: A Manual of Techniques, 1987, pp. 147-158, Chapter 6, CRC Press, Inc.

Jiang, Li-bin et al., Research Progress on Sortase and its Application in Biotechnology, Current Biotechnology, 2011, pp. 184-188, English Abstract, vol. 1, No. 3.

Thiele, Christopher S. et al., Site-specific N-terminal labeling of proteins using sortase-mediated reactions, Nature Protocols, 2013, pp. 1800-1807, vol. 8, No. 9.

JP Office action, dated Sep. 3, 2020.

Swee et al., Sortase-mediated modification of αDEC205 affords optimization of antigen presentation and immunization against a set of viral epitopes, PNAS, vol. 110, No. 4, Jan. 22, 2013, pp. 1428-1433.

\* cited by examiner

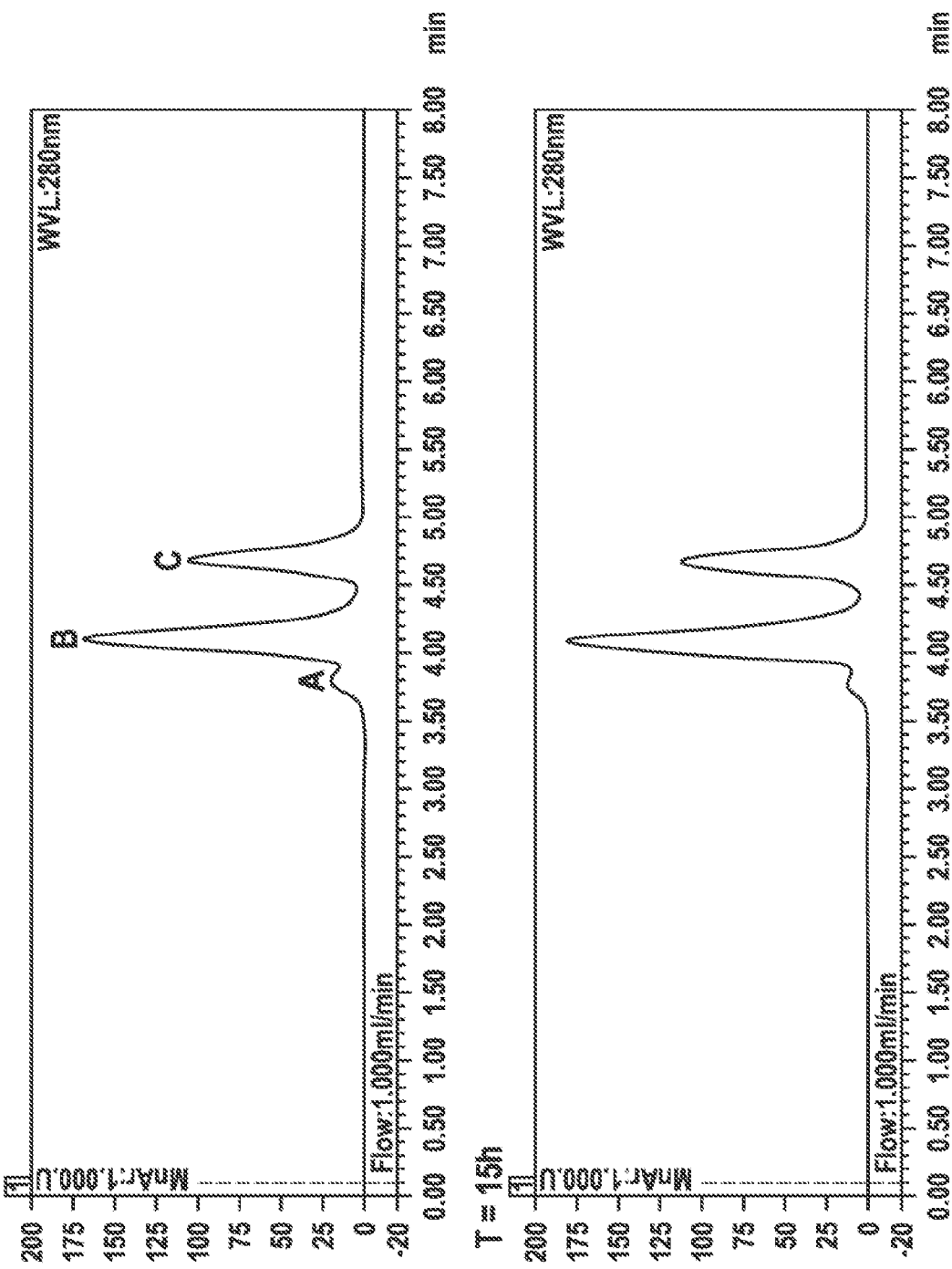

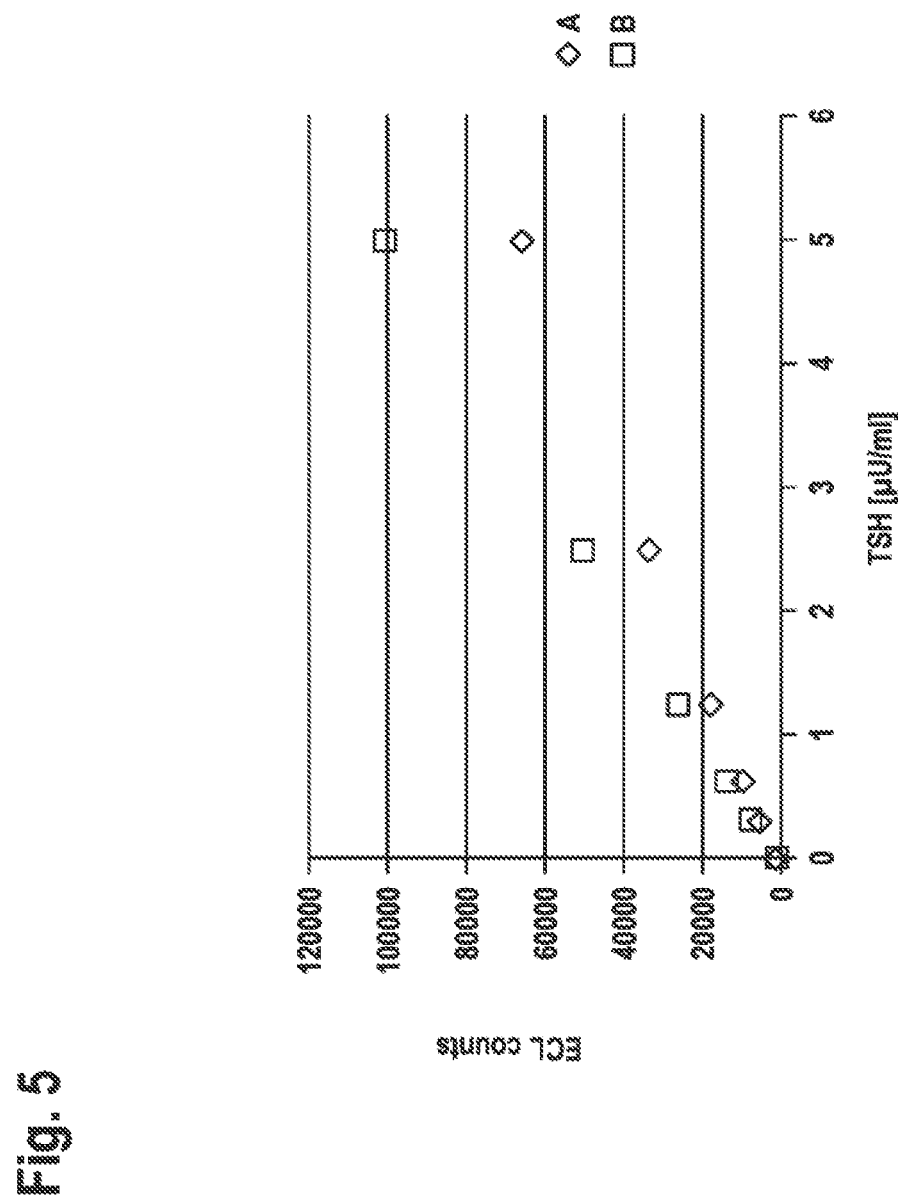

RECOMBINANT IMMUNOGLOBULIN HEAVY CHAINS COMPRISING A SORTASE CONJUGATION LOOP AND CONJUGATES THEREOF

CROSS-REFERENCE TO RELATED APPLICATIONS

This application is a continuation of International Application No. PCT/EP2016/072529 filed Sep. 22, 2016, which claims priority to European Application No. 15186821.3 filed Sep. 25, 2015, the disclosures of which are hereby incorporated by reference.

BACKGROUND OF THE INVENTION

The present invention relates to a recombinant immunoglobulin heavy chain comprising a sortase conjugation loop, to methods for conjugating and/or labeling such recombinant immunoglobulins heavy chains by use of the enzyme sortase and to the conjugates/labeled products obtained via said method.

Site-specific modification of proteins is a challenging problem especially with antibodies used for diagnostic or therapeutic applications. Reliable methods to site-specific polypeptide modification which are economic and applicable on industrial scale are of great importance.

Early methods of protein functionalization exploited the reactivity of either cysteine or lysine residues by reacting the protein with an excess of thiol- or amine-reactive reagents, such as maleimides or N-hydroxysuccinimidyl esters, respectively. They are abundant, widely distributed and easily modified due to availability of appropriate coupling chemistry.

However, the "lysine-labeling" strategy, when e.g. used to label antibodies or antigen-binding fragments thereof has several drawbacks: a) it often results in a significant decrease in the antigen-binding activity (lysine in or close to the antigen binding site); b) mono-labeled conjugates even at the same 1:1 stoichiometry consist of mixtures comprising a label attached via different ones of the lysines within the polypeptide and c) the yields of the desired 1:1 product are rather low.

One of the most important recent approaches for site-specific protein labeling is to incorporate bioorthogonal functionalities into proteins at specific sites via enzymatic reactions. For a recent review on "enzymatic labeling of proteins" see M. Rashidian et al., Bioconjugate Chemistry 24 (2013) 1277-1294. The enzymes used for site-specific conjugation covered in this review include formylglycine generating enzyme, sialyltransferases, phosphopantetheinyl-transferases, O-GlcNAc post-translational modification, sortagging, transglutaminase, farnesyltransferase, biotin ligase, lipoic acid ligase, and N-myristoyltransferase.

Sortase A (SrtA) is a membrane bound enzyme which attaches proteins covalently to the bacterial cell wall. The specific sortase recognition motif on the SrtA substrate is LPX1TX2 (SEQ ID NO: 01, wherein X1 can be any amino acid residue and X2 is G or A). The sortase enzyme cleaves between the residues threonine (T) and X2 (G or A). The ligation motif on the sortase nucleophile (also referred to as sortase substrate), i.e. the polypeptide part of the peptidoglycan that becomes attached to the substrate on the bacterial cell wall, naturally is a pentaglycine motif. It has been shown that a triglycine and even a diglycine motif on the N-terminus of the peptidoglycan is sufficient to support the SrtA reaction (Clancy, K. W., et al., Peptide Science 94 (2010) 385-396). The reaction proceeds through a thioester acyl-enzyme intermediate, which is resolved by the attack of an amine nucleophile from the oligoglycine, thereby covalently linking the peptidoglycan to a protein substrate and regenerating SrtA.

In the modern biochemical laboratory SrtA can e.g. be used to covalently conjugate chemically synthetized peptides to recombinantly expressed proteins.

In WO 2010/087994 methods for SrtA-mediated ligation and uses thereof are reported. Recombinant approaches to IgG-like bispecific antibodies are reported by Marvin, J. S., et al. (Acta Pharmacol. Sinica 26 (2005) 649-658). Levary, D. A., et al. (PLoS one, 6 (2011) e18342.1-e18342.6) showed protein-protein fusion catalyzed by sortase A. In WO 2013/003555 the use of sortases to install click chemistry handles for protein ligation is reported.

Engineering of an anti-epidermal growth factor receptor antibody to single chain format and labeling by sortase A-mediated protein ligation is reported by Madej, M. P., et al. (Biotechnol. Bioeng. 109 (2012) 1461-1470). Ta, H. T., et al., report enzymatic single-chain antibody tagging as a universal approach to targeted molecular imaging and cell homing in cardiovascular diseases (Cir. Res. 109 (2011) 365-373). Popp, M., et al., report making and breaking peptide bonds—protein engineering using sortase (Angew. Chem. Int. Ed. Eng. 50 (2011) 5024-5032).

A truncated SrtA, that lacks the N-terminal membrane-anchoring motif (e.g., amino acid residues 60-206 of *Staphylococcus aureus* SrtA), has been used for protein labeling, covalent protein immobilization and incorporation of novel functionality into proteins (Ton-That, H., et al., Proc. Natl. Acad. Sci. USA 96 (1999) 12424-12429; Ilangovan, H., et al., Proc. Natl. Acad. Sci. USA 98 (2001) 6056-6061).

One of the most important class of polypeptides for which site-specific labeling is highly desirable are the immunoglobulins or antibodies. Although whole antibodies (usually IgG, IgA or IgM) are ideal for most applications, the performance of certain procedures is enhanced by using antibody fragments, such as Fab, Fab' and F(ab')2.

The antibody fragments of primary interest are antigen-binding fragments. Several types of antigen-binding fragments are possible, but each contains at least those parts of the variable regions of both heavy and light immunoglobulin chains (VH and VL, respectively) required for antigen binding which are held together (usually by disulfide bonds) so as to preserve the antibody-binding site.

Antibody fragmentation is usually accomplished using e.g. proteases that digest or cleave certain portions of the immunoglobulin protein structure and, if necessary using reducing agents to split disulfide bonds in the hinge region of a F(ab')2 fragment. Enzymatic fragmentation is somewhat laborious, requires optimization of enzyme-mediated digestion of the protein, necessitates an ample supply of antibody (e.g., 10 mg or more) to make it reasonably efficient and often entails in addition sophisticated purification steps. The timely and costly fragmentation of an antibody is usually performed only when the antibody of interest is available in large quantity and the particular application demands it.

Antibody fragments can e.g. chemically labeled using state-of-the-art procedures, with all the disadvantages, e.g. regarding yield and reproducibility, mentioned above.

Site-directed conjugation, e.g. facilitated by enzymes, has recently received high attention.

Sortase tagging—at least on paper—could work in generating antibody fragments and "tagging" those fragments at the same time. In theory an antibody should allow for incorporation of the sortase tag, e.g. in the Fc-region of a genetically engineered recombinant antibody and to use this sortase tag for the simultaneous cleavage and conjugation. In theory and depending on the position of the sortase tag it should be possible to thus e.g. obtain conjugates of F(ab) or F(ab')2 fragments, respectively.

However, when sortase tagging was attempted with otherwise native antibodies (i.e. only the recognition sequence LPETG (SEQ ID NO:24) was inserted), like in a mouse monoclonal antibody produced by a hybridoma the approach did not work at all or the yields were low/disappointing.

A tremendous need would, however, exist, to enable sortase-mediated "tagging" of the most relevant antibody fragments like F(ab) or F(ab')2, respectively, via simultaneous cleavage and site-specific polypeptide conjugation at an economically and industrially applicable scale.

Surprisingly it has now been found that sortase can be used for conjugation of antibody-fragments (e.g. in antibody-fragment labeling) upon sortase mediated cleavage of recombinant antibody heavy chains having the properties as disclosed herein below.

SUMMARY OF THE INVENTION

It has been found that sortase-mediated cleavage and ligation of recombinant antibodies is possible if a special sortase conjugation loop is recombinantly introduced in between the C-terminal most cysteine of the middle hinge region and the CH2-domain of an immunoglobulin heavy chain.

In one embodiment the present invention discloses a recombinant immunoglobulin heavy chain comprising a VH-domain, a CH1 domain, a hinge region down to the C-terminal most cysteine of the middle hinge region, a sortase conjugation loop, a CH2 domain and a CH3 domain, wherein the sortase conjugation loop: a) consists of at least 16 amino acids located between the C-terminal most cysteine of the middle hinge region and the VFX1FPP (SEQ ID NO: 2; wherein X1 is L or I) consensus sequence at the N-terminus of an immunoglobulin heavy chain CH2-domain, b) comprises a sortase recognition motif consisting of the amino acid sequence LPX1TX2 (SEQ ID NO: 01), wherein X1 can be any amino acid residue and X2 is G or A, comprises N-terminal to the sequence of (b) at least two amino acids, comprises C-terminal to the sequence of (b) at least 6 amino acids, and wherein the amino acids C- and N-terminal to the sequence of (b) are not cysteine.

Further disclosed are antibodies comprising at least two recombinant immunoglobulin heavy chains as disclosed herein below. In one embodiments these antibodies are of the IgG class and have two recombinant immunoglobulin heavy chains as disclosed herein below.

One aspect as reported herein is a method for producing a conjugate between a sortase cleavage fragment of a recombinant immunoglobulin heavy chain and a sortase nucleophile comprising incubating i) an IgG class antibodies comprising at least one, e.g. two recombinant immunoglobulin heavy chain as disclosed in the present invention, ii) a compound comprising a sortase nucleophile, and iii) a polypeptide with sortase activity, thereby cleaving the recombinant antibody heavy chain after the threonine in LPX1TX2 (SEQ ID NO: 01, wherein X1 can be any amino acid residue and X2 is G or A) and conjugating the N-terminus of the sortase nucleophile to said threonine.

In one embodiment the present application relates a conjugate produced according to a method as disclosed herein, e.g. to a conjugate comprising a recombinant immunoglobulin heavy chain fragment comprising a VH-domain a CH1 domain a hinge region down to the last cysteine of the middle hinge region, two or more amino acids between the C-terminal most cysteine of the middle hinge region, the sequence LPXT (SEQ ID NO: 03, wherein X can be any amino acid residue) and at least two glycine residues.

DETAILED DESCRIPTION OF THE INVENTION

I. Definitions

Figure 1:
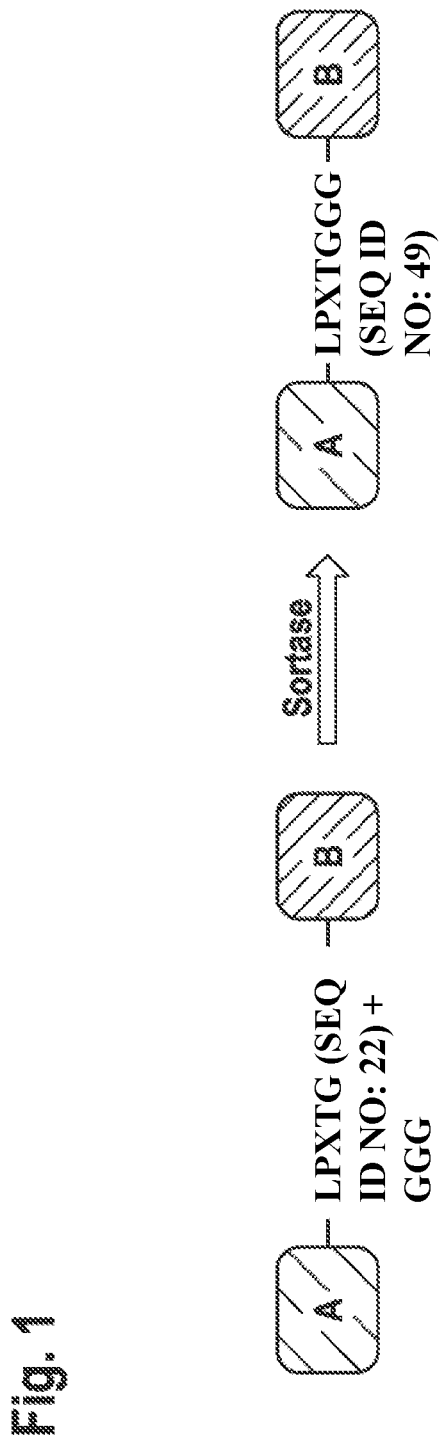
FIG. 1 Sortase reaction scheme; (A) polypeptide containing LPXTG (SEQ ID NO:22) recognizion motif; (B) sortase nucleophile.

In the present specification and claims the numbering of the residues in an immunoglobulin heavy chain Fc-region is that of the EU index of Kabat (Kabat, E. A., et al., Sequences of Proteins of Immunological Interest, 5th ed., Public Health Service, National Institutes of Health, Bethesda, Md. (1991), NIH Publication 91-3242, expressly incorporated herein by reference).

The term "position" denotes the location of an amino acid residue in the amino acid sequence of a polypeptide. Positions may be numbered sequentially, or according to an established format, for example the EU index of Kabat for antibody numbering.

The term "full length antibody" denotes an antibody that has a structure and amino acid sequence substantially identical to a native antibody.

The term "full length antibody heavy chain" denotes a polypeptide comprising in N- to C-terminal direction an antibody variable domain, a first constant domain (=CH1-domain), an antibody heavy chain hinge region, a second constant domain (=CH2-domain), and a third constant domain (=CH3-domain).

The term "full length antibody light chain" denotes a polypeptide comprising in N- to C-terminal direction an antibody variable domain and a constant domain.

The term "hinge region" denotes the part of an antibody heavy chain polypeptide that joins in a wild-type antibody heavy chain the CH1 domain and the CH2 domain, e. g. for human IgG1 from about position 216 to about position 238 according to the EU number system (www.imgt.org/IMGT-ScientificChart/Numbering/Hu_IGHGnber.html), or from about position 226 to about position 243 of Kabat numbering. Position 226 according to Kabat corresponds to position 99 of a human IgG1 heavy chain constant region. The hinge regions of other IgG subclasses can be determined by aligning with the hinge-region cysteine residues of the human IgG1 subclass sequence.

The hinge region is normally dimeric consisting of two polypeptides with identical amino acid sequence. The hinge region generally comprises about 25 amino acid residues and is flexible allowing the antigen binding regions to move independently. The hinge region can be subdivided into three domains: the upper, the middle, and the lower hinge domain (see e.g. Roux, et al., J. Immunol. 161 (1998) 4083).

The term "upper hinge region" of an Fc-region, e. g. for human IgG1, denotes the stretch of amino acid residues N-terminal to the middle hinge region, i.e. residues 216 to 225 of the Fc-region according to the EU numbering.

The term "middle hinge region", e. g. for human IgG1, i.e. residues 226 to 230 of the Fc-region according to the EU numbering, denotes the stretch of amino acid residues comprising the cross-linking cysteine residues, is rich in prolines and cysteines, and it is located between the upper and the lower hinge region.

The term "lower hinge region" of an Fc-region, e. g. for human IgG1, denotes the stretch of amino acid residues immediately C-terminal to the middle hinge region, i.e. residues 231 to 238 of the Fc-region according to the EU numbering.

The term "wild-type Fc-region" denotes an amino acid sequence identical to the amino acid sequence of an Fc-region of typical allotypes/isoallotypes found in nature. Wild-type human Fc-regions include a native human IgG1 Fc-region (non-A and A allotypes), native human IgG2 Fc-region, native human IgG3 Fc-region, and native human IgG4 Fc-region as well as naturally occurring variants thereof.

The term "alteration" denotes the mutation, addition, or deletion of one or more amino acid residues in a parent amino acid sequence, e.g. of a recombinant antibody.

The term "amino acid mutation" denotes a modification in the amino acid sequence of a parent amino acid sequence. Exemplary modifications include amino acid substitutions, insertions, and/or deletions.

The term "amino acid mutations at the position" denotes the substitution or deletion of the specified residue, or the insertion of at least one amino acid residue adjacent the specified residue. The term "insertion adjacent to a specified residue" denotes the insertion within one to two residues thereof. The insertion may be N-terminal or C-terminal to the specified residue.

The term "amino acid substitution" denotes the replacement of at least one amino acid residue in a predetermined parent amino acid sequence with a different "replacement" amino acid residue. The replacement residue or residues may be a "naturally occurring amino acid residue" (i.e. encoded by the genetic code) and selected from the group consisting of: alanine (Ala); arginine (Arg); asparagine (Asn); aspartic acid (Asp); cysteine (Cys); glutamine (Gln); glutamic acid (Glu); glycine (Gly); histidine (His); isoleucine (Ile): leucine (Leu); lysine (Lys); methionine (Met); phenylalanine (Phe); proline (Pro); serine (Ser); threonine (Thr); tryptophan (Trp); tyrosine (Tyr); and valine (Val). In one embodiment the amino acid substitution is a replacement by a naturally occurring amino acid. In one embodiment the replacement residue is not cysteine.

Substitution with one or more non-naturally occurring amino acid residues is also encompassed by the definition of an amino acid substitution herein. A "non-naturally occurring amino acid residue" denotes a residue, other than those naturally occurring amino acid residues listed above, which is able to covalently bind adjacent amino acid residues(s) in a polypeptide chain. Examples of non-naturally occurring amino acid residues include norleucine, ornithine, norvaline, homoserine, α-Aminoisobutyric acid (Aib) and other amino acid residue analogues such as those described in Ellman, et al., Meth. Enzym. 202 (1991) 301-336. To generate such non-naturally occurring amino acid residues, the procedures of Noren, et al. (Science 244 (1989) 182) and/or Ellman, et al. (supra) can be used. Briefly, these procedures involve chemically activating a suppressor tRNA with a non-naturally occurring amino acid residue followed by in vitro transcription and translation of the RNA.

The term "amino acid insertion" denotes the incorporation of one or more additional amino acid residue(s) into a predetermined parent amino acid sequence. An "inserted amino acid sequence" according to the present invention will usually consist of at least five amino acids. The inserted amino acid residue(s) may be naturally occurring or non-naturally occurring as defined above. In one embodiment the inserted amino acid residues are naturally occurring amino acid residues. In one embodiment the inserted amino acid residues are naturally occurring amino acid residues but are not cysteine. In one embodiment the inserted amino acid residues are naturally occurring amino acid residues and are neither cysteine nor proline.

The term "amino acid deletion" denotes the removal of at least one amino acid residue at a predetermined position in an amino acid sequence.

Within this application whenever an amino acid alteration is mentioned it is a deliberated amino acid alteration and not a random amino acid modification.

II. Recombinant Methods

An expression vector coding for a recombinant immunoglobulin heavy chain—comprising a VH-domain, a CH1 domain, a hinge region down to the C-terminal most cysteine of the middle hinge region, a sortase conjugation loop, a CH2 domain and a CH3 domain, wherein the sortase conjugation loop: a) consists of at least 16 amino acids located between the C-terminal most cysteine of the middle hinge region and the VFX1FPP (SEQ ID NO: 2; wherein X1 is L or I) consensus sequence at the N-terminus of an immunoglobulin heavy chain CH2-domain, b) comprises a sortase recognition motif consisting of the amino acid sequence LPX1TX2 (SEQ ID NO: 01), wherein X1 can be any amino acid residue and X2 is G or A, c) comprises N-terminal to the sequence of (b) at least two amino acids, d) comprises C-terminal to the sequence of (b) at least 6 amino acids, and e) wherein the amino acids C- and N-terminal to the sequence of (b) are not cysteine—can be manufactured according to state of the art procedures (see e.g. Sambrook, J. et al., Molecular cloning: A laboratory manual; Cold Spring Harbor Laboratory Press, Cold Spring Harbor, N.Y., 1989.)

While it is possible to use in vitro translation to produce a recombinant immunoglobulin heavy chain as disclosed herein, cellular expressions system will be used in the routine. Suitable host cells for cloning or expression/secretion of polypeptide-encoding vectors include prokaryotic or eukaryotic cells described herein. For example, polypeptides may be produced in bacteria, in particular when glycosylation is not needed (see, e.g., U.S. Pat. Nos. 5,648,237, 5,789,199 and U.S. Pat. No. 5,840,523, Charlton, Methods in Molecular Biology 248 (2003) 245-254 (B. K. C. Lo, (ed.), Humana Press, Totowa, N.J.), describing expression of antibody fragments in E. coli.). After expression, the polypeptide may be isolated from the bacterial cell paste in a soluble fraction or may be isolated from the insoluble fraction so called inclusion bodies which can be solubilized and refolded to bioactive forms. Thereafter the polypeptide can be further purified.

In addition to prokaryotes, eukaryotic microbes such as filamentous fungi or yeasts are suitable cloning or expression hosts for polypeptide-encoding vectors, including fungi and yeast strains whose glycosylation pathways have been "humanized", resulting in the production of a polypeptide with a partially or fully human glycosylation pattern (see e.g. Gerngross, Nat. Biotech. 22 (2004) 1409-1414, and Li, et al., Nat. Biotech. 24 (2006) 210-215).

Suitable host cells for the expression of glycosylated polypeptides are also derived from multicellular organisms (invertebrates and vertebrates). Examples of invertebrate cells include plant and insect cells. Numerous baculoviral strains have been identified which may be used in conjunction with insect cells, particularly for transfection of Spodoptera frugiperda cells.

Plant cell cultures can also be utilized as hosts (see, e.g., U.S. Pat. Nos. 5,959,177, 6,040,498, U.S. Pat. Nos. 6,420,548, 7,125,978 and 6,417,429 (describing PLANTIBODIES™ technology for producing antibodies in transgenic plants)).

Vertebrate cells may also be used as hosts. For example, mammalian cell lines that are adapted to grow in suspension may be useful. Other examples of useful mammalian host cell lines are the COS-7 cell line (monkey kidney CV1 cell transformed by SV40); the HEK293 cell line (human embryonic kidney); the BHK cell line (baby hamster kidney); the TM4 mouse sertoli cell line (TM4 cells as described, e.g., in Mather, Biol. Reprod. 23 (1980) 243-251); the CV1 cell line (monkey kidney cell); the VERO-76 cell line (African green monkey kidney cell); the HELA cell line (human cervical carcinoma cell); the MDCK cell line (canine kidney cell); the BRL-3A cell line (buffalo rat liver cell); the W138 cell line (human lung cell); the HepG2 cell line (human liver cell); the MMT 060562 cell line (mouse mammary tumor cell); the TRI cell line (e.g. described in Mather, et al., Anal. N.Y. Acad. Sci. 383 (1982) 44-68); the MRCS cell line; and the FS4 cells-line. Other useful mammalian host cell lines include the CHO cell line (Chinese hamster ovary cell), including DHFR negative CHO cell lines (see e.g. Urlaub, et al., Proc. Natl. Acad. Sci. USA 77 (1980) 4216), and myeloma cell lines such as Y0, NS0 and Sp2/0 cell line. For a review of certain mammalian host cell lines suitable for polypeptide production, see, e.g., Yazaki, and Wu, Methods in Molecular Biology, Antibody Engineering 248 (2004) 255-268 (B. K. C. Lo, (ed.), Humana Press, Totowa, N.J.).

Co-expression of an antibody heavy chain and an antibody light chain represents one embodiment according to the present disclosure. Using such co-expression an antibody comprising both, a heavy and a light chain can be obtained, e.g. an IgG-class antibody consisting of two recombinant heavy chains according to the present invention and two light chains.

III. The Recombinant Antibody Heavy Chain and Uses Thereof as Reported Herein

The recombinant immunoglobulin heavy chain according to the present invention is characterized by the purposeful insertion of a sortase conjugation loop.

The sortase conjugation loop according to the present invention is an artificial amino acid sequence located between the C-terminal most cysteine of the middle hinge region and the VFX1FPP (SEQ ID NO: 2; wherein X1 is L or I) consensus sequence at the N-terminus of an immunoglobulin heavy chain CH2-domain. The sortase conjugation loop according to the present invention additionally has the following essential characteristics: a) it consists of at least 16 amino acids b) it comprises a sortase recognition motif consisting of the amino acid sequence LPX1TX2 (SEQ ID NO: 01), wherein X1 can be any amino acid residue and X2 is G or A, c) it comprises N-terminal to the sequence of (b) at least two amino acids, d) it comprises C-terminal to the sequence of (b) at least 6 amino acids, and e) the amino acids C- and N-terminal to the sequence of (b) are not cysteine As shown in Table 1 the middle hinge region of various immunoglobulin heavy chains can be easily identified via appropriate sequence alignment. The C-terminal most cysteine in the middle hinge region is indicated in bold in Table 1. In the Table 1 typical sequence alignments of consensus sequences for immunoglobulin heavy chains from various species are given.

TABLE 1

Exemplary consensus sequences for various immunoglobulin heavy chains

| Isotype | C-terminus of CH1 | Upper- and middle-hinge | lower hinge and N-terminus of CH2 |
|---|---|---|---|
| H(human)-IgG1 (SEQ ID NO: 4) | TKVDKKV (SEQ ID NO: 26) | EPKSCDK-THT-CPPC------P (SEQ ID NO: 31) | APELLGGPSVFLF (SEQ ID NO: 16) |
| H-IgG2 (SEQ ID NO: 5) | TKVDKKV (SEQ ID NO: 26) | ERK-CCVE----CPPC------P (SEQ ID NO: 32) | APP-VAGPSVFLF (SEQ ID NO: 40) |
| H-IgG4 (SEQ ID NO: 6) | TKVDKRV (SEQ ID NO: 14) | ESKY-----GPPCPSC------P (SEQ ID NO: 33) | APEFLGGPSVFLF (SEQ ID NO: 40) |
| M-IgG1 (SEQ ID NO: 7) | TKVDKKI (SEQ ID NO: 27) | VPRDC------GCKPCI----CT (SEQ ID NO: 20) | VPEV---SSVFIF (SEQ ID NO: 41) |
| M(mouse)-IgG2a (a) (SEQ ID NO: 8) | TKVDKKI (SEQ ID NO: 27) | EPRGP---TIKPCPPCK----CP (SEQ ID NO: 34) | APNLLGGPSVFIF (SEQ ID NO: 43) |

TABLE 1-continued

Exemplary consensus sequences for various immunoglobulin heavy chains

| Isotype | C-terminus of CH1 | Upper- and middle-hinge | lower hinge and N-terminus of CH2 |
|---|---|---|---|
| M-IgG2a(b) (SEQ ID NO: 9) | TKVDKKI (SEQ ID NO: 27) | EPRVPI--TQNPCPPLKECPPCA (SEQ ID NO: 35) | APDLLGGPSVFIF (SEQ ID NO: 44) |
| M-IgG2b (SEQ ID NO: 10) | TTVDKKL (SEQ ID NO: 28) | EPSGPI-STINPCPPCKECHKCP (SEQ ID NO: 36) | APNLEGGPSVFIF (SEQ ID NO: 45) |
| M-IgG3 (SEQ ID NO: 11) | TELIKRI (SEQ ID NO: 29) | EPRIPKPST----PPGSS---CP (SEQ ID NO: 37) | AGNILGGPSVFIF (SEQ ID NO: 46) |
| Rb(rabbit)-IgG (SEQ ID NO: 12) | TKVDKTV (SEQ ID NO: 30) | APSTCSKPT-----------CP (SEQ ID NO: 38) | PPELLGGPSVFIF (SEQ ID NO: 47) |
| S(sheep)-IgG (SEQ ID NO: 13) | TKVDKRV (SEQ ID NO: 14) | EPGCPD-----PCKHCR----CP (SEQ ID NO: 39) | PPELPGGPSVFIF (SEQ ID NO: 48) |

The sequence parts shown in Table 1 are given under the following sequence identifiers: H-IgG1 (SEQ ID NO: 4); H-IgG2 (SEQ ID NO: 5); H-IgG4 (SEQ ID NO: 6); M-IgG1 (SEQ ID NO: 7); M-IgG2a(a) (SEQ ID NO: 8); M-IgG2a(b) (SEQ ID NO: 9); M-IgG2b (SEQ ID NO: 10); M-IgG3 (SEQ ID NO: 11); Rb-IgG (SEQ ID NO: 12); and S-IgG (SEQ ID NO: 13), respectively.

A special case is H-IgG3, wherein the upper/middle hinge region comprises 3 replicates of an identical sequence and one additional highly homologous sequence. The C-terminus of CH1 is; TKVDKRV (SEQ ID NO: 14); the upper- and middle-hinge is ELKTPLGDTTHTCPRCP (EPKSCDTPPPCPRPC)3 (SEQ ID NO: 15); and the lower hinge with the N-terminal amino acids of the CH2-domain is APELLGGPSVFLF(SEQ ID NO: 16).

The hinge region of an antibody spans the part of the heavy chain sequence between the last amino acid of the most C-terminal β-sheet in the CH1-domain (G-strand) and the first amino acid of the first β-sheet in the CH2-domain (A-strand).

The sequence of the upper hinge region (whether native or modified) is not critical to practice the present invention.

The middle hinge region comprises the cysteine residues that are required for formation of an inter-molecular cystine bridge between two immunoglobulin heavy chains.

In one embodiment the recombinant immunoglobulin heavy chain according to the present disclosure has a sortase conjugation loop comprising at least 7 amino acids C-terminal to the sequence LPX1TX2 (SEQ ID NO: 01, wherein X1 can be any amino acid residue and X2 is G or A).

In one embodiment the recombinant immunoglobulin heavy chain according to the present disclosure has a sortase conjugation loop comprising at least 8 amino acids C-terminal to the sequence LPX1TX2 (SEQ ID NO: 01, wherein X1 can be any amino acid residue and X2 is G or A).

In one embodiment the recombinant immunoglobulin heavy chain according to the present disclosure has a sortase conjugation loop comprising at least 9 amino acids C-terminal to the sequence LPX1TX2 (SEQ ID NO: 01, wherein X1 can be any amino acid residue and X2 is G or A).

In one embodiment the recombinant immunoglobulin heavy chain according to the present disclosure has a sortase conjugation loop comprising at least 3 amino acids N-terminal to the sequence LPX1TX2 (SEQ ID NO: 01, wherein X1 can be any amino acid residue and X2 is G or A).

In one embodiment the recombinant immunoglobulin heavy chain according to the present disclosure has a sortase conjugation loop comprising at least 4 amino acids N-terminal to the sequence LPX1TX2 (SEQ ID NO: 01, wherein X1 can be any amino acid residue and X2 is G or A).

In one embodiment the recombinant immunoglobulin heavy chain according to the present disclosure has a sortase conjugation loop comprising at least 5 amino acids N-terminal to the sequence LPX1TX2 (SEQ ID NO: 01, wherein X1 can be any amino acid residue and X2 is G or A).

In one embodiment the recombinant immunoglobulin heavy chain according to the present disclosure has a sortase conjugation loop comprising at least 6 amino acids N-terminal to the sequence LPX1TX2 (SEQ ID NO: 01, wherein X1 can be any amino acid residue and X2 is G or A).

In one embodiment the recombinant immunoglobulin heavy chain according to the present disclosure has a sortase conjugation loop comprising at least 7 amino acids N-terminal to the sequence LPX1TX2 (SEQ ID NO: 01, wherein X1 can be any amino acid residue and X2 is G or A).

In one embodiment the recombinant immunoglobulin heavy chain according to the present disclosure has a sortase conjugation loop comprising at least 8 amino acids N-terminal to the sequence LPX1TX2 (SEQ ID NO: 01, wherein X1 can be any amino acid residue and X2 is G or A).

In one embodiment the recombinant immunoglobulin heavy chain according to the present disclosure has a sortase conjugation loop comprising at least 5 amino acids N-terminal to the sequence LPX1TX2 (SEQ ID NO: 01, wherein X1 can be any amino acid residue and X2 is G or A) and at least 9 amino acids C-terminal to said sequence.

In one embodiment the recombinant immunoglobulin heavy chain according to the present disclosure has a sortase conjugation loop comprising at least 8 amino acids N-terminal to the sequence LPX1TX2 (SEQ ID NO: 01, wherein X1 can be any amino acid residue and X2 is G or A) and at least 9 amino acids C-terminal to said sequence.

As long as the minimal length of 16 amino acids according to the present disclosure is respected, the overall length of a sortase conjugation loop does not appear to be critical. Nonetheless, in one embodiment the sortase conjugation loop in a recombinant immunoglobulin heavy chain according to the present disclosure is at most 50 amino acids long. In further embodiments the sortase conjugation loop in a recombinant immunoglobulin heavy chain according to the present disclosure is at most 45, 40, 35 or 30 amino acids long.

In further embodiments the overall length of a sortase conjugation loop is at least 17, 18, 19, 20, 21 or 22 amino acids, respectively.

An immunoglobulin heavy chain usually comprises a VH-domain, a CH1 domain, a hinge region, a CH2 domain and a CH3 domain. As the skilled artisan appreciates in a recombinant immunoglobulin heavy chain according to the present invention in addition to the sortase conjugation loop may comprise further alterations as defined herein above. As the name indicates, the variable sequence can be varied in any manner, as long as the desired binding specificity to a target of interest is given. In one embodiment the recombinant antibody heavy chain comprising a sortase conjugation loop according to the present invention will be at least 90% identical to the corresponding naturally occurring immunoglobulin heavy chain (wherein the lower hinge region and the sortase conjugation loop, respectively are not used in such assessment of identity). With other words, after appropriate alignment using the GCG PileUp program and except for variable regions and the sortase conjugation loop on the one hand and the lower hinge region on the other hand, a recombinant immunoglobulin heavy chain is at least 90% identical to the (corresponding) consensus sequence for said immunoglobulin heavy chains. In other embodiments the identity of a recombinant immunoglobulin heavy chain will be each at least 95%, at least 97%, at least 98%, or at least 99% as compared to the corresponding consensus sequence. In one embodiment each of the CH1-domain, CH2-domain and the CH3-domain sequences of a recombinant immunoglobulin heavy chain according to the present invention will be at least to 90% identical to the corresponding naturally occurring immunoglobulin heavy chain. With other words, after appropriate alignment using the GCG PileUp program, at least 90% of the amino acids of e.g. such altered CH1-domain of a recombinant mouse IgG1 heavy chain are identical to the (corresponding) amino acids of the consensus sequence for the mouse IgG1 heavy chain CH1-domain. In other embodiments the identity of a modified CH1-domain, CH2-domain and CH3-domain, respectively, will be each at least 95%, at least 97%, at least 98%, or at least 99% as compared to the corresponding consensus sequence.

As mentioned above, co-expression of an antibody heavy chain and an antibody light chain represents one embodiment according to the present disclosure. Using such co-expression, especially in connection with a cellular expression system, an antibody comprising both, a heavy and a light chain can be obtained. The co-expression of a (recombinant) immunoglobulin heavy chain and its corresponding light chain leads to both the formation of the desired antibody as well as to a high production yield.

There are various isotypes of human antibodies, e.g., referred to as alpha immunoglobulins (=IgAs), gamma-immunoglobulins (=IgGs), delta immunoglobulins (IgDs), epsilon immunoglobulins (IgEs) and my immunoglobulins (IgMs). In one embodiment the present disclosure relates to an antibody (of any of these isotypes or the corresponding isotypes from other species, or their corresponding subclasses), comprising at least two recombinant immunoglobulin heavy chains as disclosed in the present application.

In one embodiment an IgG class antibody is described and claimed having two recombinant immunoglobulin heavy chains as disclosed in the present application.

As the name already suggests, a recombinant antibody heavy chain comprising a sortase conjugation loop according to the present invention can be used in sortase ligation-based methods.

In one embodiment the present disclosure relates to a method for producing a conjugate of a sortase cleavage fragment of a recombinant immunoglobulin heavy chain and a sortase nucleophile the method comprising incubating i) an antibody comprising at least two recombinant immunoglobulin heavy chains each comprising a sortase conjugation loop wherein the sortase conjugation loop a) consists of at least 16 amino acids located between the C-terminal most cysteine of the middle hinge region and the VFX1FPP (SEQ ID NO: 2; wherein X1 is L or I) consensus sequence at the N-terminus of an immunoglobulin heavy chain CH2-domain, b) comprises a sortase recognition motif consisting of the amino acid sequence LPX1TX2 (SEQ ID NO: 01), wherein X1 can be any amino acid residue and X2 is G or A, c) comprises N-terminal to the sequence of (b) at least two amino acids, d) comprises C-terminal to the sequence of (b) at least 6 amino acids, and e) wherein the amino acids C- and N-terminal to the sequence of (b) are not cysteine ii) a compound comprising a sortase nucleophile, and iii) a polypeptide with sortase activity, thereby cleaving the recombinant antibody heavy chain after the threonine in LPX1TX2 (SEQ ID NO: 01, wherein X1 can be any amino acid residue and X2 is G or A) and conjugating the N-terminus of the sortase nucleophile to said threonine.

As the skilled artisan will readily appreciate, such incubation will be performed using buffer conditions appropriate to achieve the desired result, i.e. the desired conjugate. Such appropriate conditions are well-known from the literature and standard sortase ligation buffers e.g. comprise $MgCl_2$.

Sortase A (SrtA) is a membrane bound enzyme which attaches proteins covalently to the bacterial cell wall. The specific "sortase recognition motif" or "sortase motif" is LPX1TX2 (SEQ ID NO: 01, wherein X1 can be any amino acid residue and X2 is G or A). In one embodiment the sortase recognition motif is LPX1TX2 wherein X2 is G. In one embodiment X1 is a naturally occurring amino acid. In one embodiment X1 is not a cysteine residue. In one embodiment X1 is a naturally occurring amino acid and is not a cysteine residue Many gram-positive bacteria use sortase to covalently anchor a variety of surface proteins including virulence factors to their cell wall (peptidoglycan). Sortases are membrane associated enzymes. The wild-type *Staphylococcus aureus* sortase A (SrtA) is a polypeptide of 206 amino acids with an N-terminal membrane-spanning region. In a first step, sortase A recognizes substrate proteins that contain a sortase recognition motif (LPX1TX2 (SEQ ID NO: 01, wherein X1 can be any amino acid residue and X2 is G or A). The sortase enzyme cleaves between the residues threonine (T) and X2 (G or A). Enzymatic cleavage of the amide bond after Thr is by means of an active-site Cys. This peptide cleaving reaction results in a sortase A-substrate thioester intermediate. In a second step the thioester acyl-enzyme intermediate is resolved by nucleophilic attack of an amino group in the sortase substrate (sortase nucleophile) comprising a sortase ligation motif. In nature the sortase substrate polypeptide corresponds to the pentaglycine unit of peptidoglycan in *S. aureus* and the nucleophilic attack leads to a covalently linked cell wall protein and the regeneration of sortase A. In the absence of oligoglycine nucleophiles, the acyl-enzyme intermediate can be hydrolyzed by a water molecule.

The "sortase nucleophile" comprises a "sortase ligation motif" or simply "ligation motif" and a "tag of interest" or simply "tag". The sortase nucleophile has N-terminally an oligoglycine and consists of at least two glycine residues as its ligation motif. With other words, the sortase ligation motif consists of at least two consecutive glycine residues.

In one embodiment the method according to the present application is practiced using a sortase nucleophile comprising the tag of interest having the formula (Gly)n-tag, wherein n is at least 2. The sortase ligation motif (Gly)$_n$ may be longer and may consist of 3, 4, 5, or 6 glycine residues, i.e. n in Gly)n-tag is 3, 4, 5, or 6. In further embodiments the method according to the present application is practiced using a sortase nucleophile comprising the tag of interest having the formula (Gly)n-tag, wherein n is 3, 4, 5, or 6, respectively.

In nature the sortase ligation motif on the peptidoglycan is a pentaglycine motif. It has been shown that a triglycine and even a diglycine motif on the N-terminus is sufficient to support the SrtA reaction (Clancy, K. W., et al., Peptide Science 94 (2010) 385-396). The reaction proceeds through a thioester acyl-enzyme intermediate, which is resolved by the attack of an amine nucleophile from the oligoglycine, covalently linking peptidoglycan to a protein substrate and regenerating SrtA. SrtA can e.g. be used to covalently conjugate chemically synthetized peptides or peptide containing substrates comprising a ligation motif to recombinantly expressed proteins comprising a sortase recognition motif.

Sortase-mediated ligation/conjugation has begun to be applied for a variety of protein engineering and bioconjugation purposes. This technique enables the introduction of natural and synthetic functionalities into LPX1TX2 (SEQ ID NO:01)-tagged recombinant or chemically synthesized polypeptides. Examples include the covalent attachment of oligoglycine derivatized polymers (e.g. PEG), fluorophores, vitamins (e.g. biotin and folate), lipids, carbohydrates, nucleic acids, synthetic peptides and proteins (e.g. GFP) (see e.g. Tsukiji, S. and Nagamune, T., ChemBioChem 10 (2009) 787-798; Popp, M. W. L. and Ploegh, H. L., Angew. Chem. Int. Ed. Engl. 50 (2011) 5024-5032).

For the enzymatic conjugation in vitro in one embodiment a soluble truncated sortase A lacking the membrane-spanning region (SrtA; amino acid residues 60-206 of *Staphylococcus aureus* SrtA) is used (SEQ ID NO: 17; Ton-That, H., et al., Proc. Natl. Acad. Sci. USA 96 (1999) 12424-12429; Ilangovan, H., et al., Proc. Natl. Acad. Sci. USA 98 (2001) 6056-6061).

The "tag of interest" or simply the "tag" comprised in the sortase nucleophile can be a partner of a binding pair, a functional group, a therapeutic agent (drug), a cytotoxic agent (e.g. a toxin such as doxorubicin or pertussis toxin) and a label (e.g. a fluorophore such as a fluorescent dye like fluorescein or rhodamine, a chemiluminescent or an electrochemiluminescent label, a radioactive label, a metal chelate complex for imaging or radiotherapeutic purposes, an enzyme or a fluorescent protein like GFP).

In one embodiment the tag is a partner of a binding pair. A binding pair as used herein consists of two partners binding to each other with high affinity, i.e. with one nanomolar affinity or better. Embodiments for binding pairs are for example the binding pairs consisting of receptor and ligand, hapten and anti-hapten antibody, and binding pairs based on naturally occurring high affinity binding pairs.

One example of a receptor-ligand binding pair is a pair consisting of a steroid hormone receptor and the corresponding steroid hormone.

One type of a binding pair which is suitable for the method according to the present invention is a hapten and anti-hapten antibody binding pair. A hapten is an organic molecule with a molecular weight of 100 to 2000 Dalton, preferably of 150 to 1000 Dalton. Such small molecule can be rendered immunogenic by coupling it to a carrier molecule and anti-hapten antibodies can be generated according to standard procedures. The hapten may be selected from the group comprising sterols, bile acids, sexual hormones, corticoids, cardenolides, cardenolide-glycosides, bufadienolides, steroid-sapogenines and steroid alkaloids, cardenolides and cardenolide-glycosides. Representatives of these substance classes are digoxigenin, digitoxigenin, gitoxigenin, strophanthidin, digoxin, digitoxin, ditoxin, strophanthin. Another suitable hapten is for example fluorescein.

Examples of binding pairs based on naturally occurring high affinity binding pairs are biotin or biotin analogues such as aminobiotin, iminobiotin or desthiobiotin and avidin or streptavidin as well as the FimG and DsF binding pair. The biotin-(strept)avidin binding pair is well-known in the art. The basic principles of the FimG-DsF binding pair are e.g. described in WO2012/028697.

In one embodiment binding pairs are selected from hapten and anti-hapten antibody, biotin or biotin analogues such as aminobiotin, iminobiotin or desthiobiotin and avidin or streptavidin, FimG and DsF, and receptor and ligand.

In one embodiment binding pairs are selected from hapten and anti-hapten antibody and biotin or biotin analogues such as aminobiotin, iminobiotin or desthiobiotin/avidin or streptavidin, FimG and DsF.

In one embodiment the binding pair is biotin (or biotin analogues such as aminobiotin, iminobiotin or desthiobiotin) and avidin or streptavidin.

In one embodiment the binding pair consists of biotin and streptavidin.

In one embodiment the tag is a functional group selected from the group consisting of aldehyde, carboxylic acid, carboxylic acid ester, epoxide, N-hydroxysuccinimide ester, amino group, halogen, hydrazine, hydroxyl, sulfhydryl, maleimido, alkynyl, azide, isocyanate, isothiocyanate and phosphoramidite, trans-cyclooctene, tetrazine.

In one embodiment the tag is a functional group selected from the group consisting of carboxylic acid, N-hydroxysuccinimide ester, amino group, halogen, sulfhydryl, maleimido, alkynyl, azide, isocyanate, isothiocyanate and phosphoramidite.

The tag may be a therapeutic agent (drug) and may e.g. be an antibody or an antigen-binding fragment thereof. A number of therapeutic antibodies directed against cell surface molecules and their ligands are known, such as Rituxan/MabThera/Rituximab, 2H7/Ocrelizumab, Zevalin/Ibrizumomab, Arzerra/Ofatumumab (CD20), HLL2/Epratuzumab, Inotuzomab (CD22), Zenapax/Daclizumab, Simulect/Basiliximab (CD25), Herceptin/Trastuzumab, Pertuzumab (Her2/ERBB2), Mylotarg/Gemtuzumab (CD33), Raptiva/Efalizumab (Cd11a), Erbitux/Cetuximab (EGFR, epidermal growth factor receptor), IMC-1121B (VEGF receptor 2), Tysabri/Natalizumab (α4-subunit of α4β1 and α4β7 integrins), ReoPro/Abciximab (gpIIb-gpIIa and αvβ3-integrin), Orthoclone OKT3/Muromonab-CD3 (CD3), Benlysta/Belimumab (BAFF), Tolerx/Oteliximab (CD3), Soliris/Eculizumab (C5 complement protein), Actemra/Tocilizumab (IL-6R), Panorex/Edrecolomab (EpCAM, epithelial cell adhesion molecule), CEA-CAM5/Labetuzumab (CD66/CEA, carcinoembryonic antigen), CT-11 (PD-1, programmed death-1 T-cell inhibitory receptor, CD-d279), H224G11 (c-Met receptor), SAR3419 (CD19), IMC-A12/

Cixutumumab (IGF-1R, insulin-like growth factor 1 receptor), MEDI-575 (PDGF-R, platelet-derived growth factor receptor), CP-675, 206/Tremelimumab (cytotoxic T lymphocyte antigen 4), RO5323441 (placenta growth factor or PGF), HGS1012/Mapatumumab (TRAIL-R1), SGN-70 (CD70), Vedotin(SGN-35)/Brentuximab (CD30), and ARH460-16-2 (CD44).

The tag may also be a cytotoxic agent selected from: (i) chemotherapeutic agents, which may function as microtubule inhibitors, mitosis inhibitors, topoisomerase inhibitors, or DNA intercalators; (ii) protein toxins, which may function enzymatically; and (iii) therapeutic radioisotopes.

Exemplary chemotherapeutic agents include, but are not limited to, a maytansinoid, an auristatin, a dolastatin, a trichothecene, CC1065, a calicheamicin and other enediyne antibiotics, a taxane, an anthracycline, and stereoisomers, isosters, analogs or derivatives thereof.

Protein toxins include diphtheria-A chain, non-binding active fragments of diphtheria toxin, exotoxin A chain (from *Pseudomonas aeruginosa*), ricin A chain (Vitetta et al (1987) Science, 238:1098), abrin A chain, modeccin A chain, alpha-sarcin, *Aleurites fordii* proteins, dianthin proteins, *Phytolaca americana* proteins (PAPI, PAPII, and PAP-5), *Momordica charantia* inhibitor, curcin, crotin, *Sapaonaria officinalis* inhibitor, gelonin, mitogellin, restrictocin, phenomycin, enomycin, and the tricothecenes (WO 93/21232).

Therapeutic radioisotopes include 32P, 33P, 90Y, 125I, 131I, 131In, 153Sm, 186Re, 188Re, 211At, 212B, 212Pb, and radioactive isotopes of Lu.

The radioisotope may be incorporated in known ways (Fraker et al (1978) Biochem. Biophys. Res. Commun. 80: 49-57; "Monoclonal Antibodies in Immunoscintigraphy" Chatal, CRC Press 1989).

Carbon-14-labeled 1-isothiocyanatobenzyl-3-methyldiethylene triamine pentaacetic acid (MX-DTPA) is an exemplary chelating agent for conjugation of a radionuclide to the complex (WO 94/11026).

In one embodiment the tag is a label. Any label moiety which can be covalently attached to the sortase ligation motif amino acid sequence can be used (see e.g. Singh et al (2002) Anal. Biochem. 304:147-15; Harlow E. and Lane, D. (1999) Using Antibodies: A Laboratory Manual, Cold Springs Harbor Laboratory Press, Cold Spring Harbor, N.Y.; Lundblad R. L. (1991) Chemical Reagents for Protein Modification, 2nd ed. CRC Press, Boca Raton, Fla.). The label may function to: (i) provide a detectable signal; (ii) interact with a second label to modify the detectable signal provided by the first or second label, e.g. to give FRET (fluorescence resonance energy transfer); (iii) affect mobility, e.g. electrophoretic mobility or cell-permeability, by charge, hydrophobicity, shape, or other physical parameters, or (iv) provide a capture moiety, e.g. to modulate ionic complexation.

Numerous labels are available which can be generally grouped into the following categories:

(a) Fluorescent dyes, chemiluminescent dyes (Briggs et al "Synthesis of Functionalized Fluorescent Dyes and Their Coupling to Amines and Amino Acids," J. Chem. Soc., Perkin-Trans. 1 (1997) 1051-1058) and electrochemiluminescent labels provide a detectable signal and are generally applicable for labeling.

Fluorescent labels or fluorophores include rare earth chelates (europium chelates), fluorescein type labels including FITC, 5-carboxyfluorescein, 6-carboxy fluorescein; rhodamine type labels including TAMRA; dansyl; Lissamine; cyanines; phycoerythrins; Texas Red; and analogs thereof. The fluorescent labels can be conjugated to the sortase ligation motif using the techniques disclosed in Current Protocols in Immunology, supra, for example. Fluorescent dyes and fluorescent label reagents include those which are commercially available from Invitrogen/Molecular Probes (Eugene, Oreg., USA) and Pierce Biotechnology, Inc. (Rockford, Ill.).

The different classes of chemiluminogenic labels include luminol, acridinium compounds, coelenterazine and analogues, dioxetanes, systems based on peroxyoxalic acid and their derivatives. For immunodiagnostic procedures predominantly acridinium based labels are used (a detailed overview is given in Dodeigne C. et al., Talanta 51 (2000) 415-439).

The tags of major relevance as electrochemiluminescent labels are the Ruthenium- and the Iridium-based electrochemiluminescent complexes, respectively. Electrochemiluminescense (ECL) proved to be very useful in analytical applications as a highly sensitive and selective method. It combines analytical advantages of chemiluminescent analysis (absence of background optical signal) with ease of reaction control by applying electrode potential. In general Ruthenium complexes, especially [Ru (Bpy)3]2+(which releases a photon at ~620 nm) regenerating with TPA (Tripropylamine) in liquid phase or liquid-solid interface are used as ECL-labels. Recently also Iridium-based ECL-labels have been described (WO2012107419(A1)).

(b) Radioactive labels make use of radioisotopes (radionuclides), such as 3H, 11C, 14C, 18F, 32P, 35S, 64Cu, 68Gn, 86Y, 89Zr, 99TC, 111In, 123I, 124I, 125I, 131I, 133Xe, 177Lu, 211At, or 131Bi.

(c) Metal-chelate complexes suitable as labels for imaging and therapeutic purposes are well-known in the art (US 2010/0111856; U.S. Pat. Nos. 5,342,606; 5,428,155; 5,316, 757; 5,480,990; U.S. Pat. Nos. 5,462,725; 5,428,139; 5,385, 893; 5,739,294; 5,750,660; 5,834,456; Hnatowich et al, J. Immunol. Methods 65 (1983) 147-157; Meares et al, Anal. Biochem. 142 (1984) 68-78; Mirzadeh et al, Bioconjugate Chem. 1 (1990) 59-65; Meares et al, J. Cancer (1990), Suppl. 10:21-26; Izard et al, Bioconjugate Chem. 3 (1992) 346-350; Nikula et al, Nucl. Med. Biol. 22 (1995) 387-90; Camera et al, Nucl. Med. Biol. 20 (1993) 955-62; Kukis et al, J. Nucl. Med. 39 (1998) 2105-2110; Verel et al., J. Nucl. Med. 44 (2003) 1663-1670; Camera et al, J. Nucl. Med. 21 (1994) 640-646; Ruegg et al, Cancer Res. 50 (1990) 4221-4226; Verel et al, J. Nucl. Med. 44 (2003) 1663-1670; Lee et al, Cancer Res. 61 (2001) 4474-4482; Mitchell, et al, J. Nucl. Med. 44 (2003) 1105-1112; Kobayashi et al Bioconjugate Chem. 10 (1999) 103-111; Miederer et al, J. Nucl. Med. 45 (2004) 129-137; DeNardo et al, Clinical Cancer Research 4 (1998) 2483-90; Blend et al, Cancer Biotherapy & Radiopharmaceuticals 18 (2003) 355-363; Nikula et al J. Nucl. Med. 40 (1999) 166-76; Kobayashi et al, J. Nucl. Med. 39 (1998) 829-36; Mardirossian et al, Nucl. Med. Biol. 20 (1993) 65-74; Roselli et al, Cancer Biotherapy & Radiopharmaceuticals, 14 (1999) 209-20).

(d) Enzymes also may be used as a tag/label in a sortase nucleophile. Various enzyme-substrate label systems are available. The enzyme generally catalyzes a chemical alteration of a chromogenic substrate that can be measured using various techniques. For example, the enzyme may catalyze a color change in a substrate, which can be measured spectrophotometrically. Alternatively, the enzyme may alter the fluorescence or chemiluminescence of the substrate. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRP), alkaline phosphatase (AP), (3-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like.

Examples of enzyme-substrate combinations (see also U.S. Pat. Nos. 4,275,149; 4,318,980) include, for example:

(i) Horseradish peroxidase (HRP) with hydrogen peroxidase as a substrate, wherein the hydrogen peroxidase oxidizes a dye precursor (e.g., orthophenylene diamine (OPD) or 3,3',5,5'-tetramethylbenzidine hydrochloride (TMB));

(ii) alkaline phosphatase (AP) with para-nitrophenyl phosphate as chromogenic substrate; and (iii) (3-D-galactosidase ((3-D-Gal) with a chromogenic substrate (e.g., p-nitro phenyl-(3-D-galactosidase) or fluorogenic substrate 4-methylumbelliferyl-(3-D-galactosidase.

In one embodiment the present invention relates to a conjugate produced according to any of the methods disclosed herein.

In one embodiment the conjugate produced according to a method as described herein will comprise a recombinant immunoglobulin heavy chain fragment comprising a VH-domain a CH1 domain a hinge region down to the last cysteine of the middle hinge region, two or more amino acids between the C-terminal most cysteine of the middle hinge region, the sequence LPXT (SEQ ID NO: 03, wherein X can be any amino acid residue) and at least two glycine residues.

As mentioned herein above it is advantageous to produce complete antibodies, i.e. antibodies having both a recombinant immunoglobulin heavy chain as disclosed herein and an immunoglobulin light chain. In case such antibody is used in a method according to the present disclosure (in "sortagging") F(ab')2-like fragments are obtained. These F(ab')2-like fragments closely resemble the F(ab')2-fragments obtained via standard procedures. If the same antibody comprising a recombinant heavy chain as disclosed herein would be used in a standard procedure or in a sortagging procedure, the sequences would be identical down to the last cysteine but would be significantly different regarding the amino acids C-terminal to the last cysteine of the middle hinge region, i.e. one procedure resulting in standard F(ab')2-fragments, the other (sortagging) resulting in quite similar but not identical F(ab')2-like fragments. After sortagging these F(ab')2-like fragments obviously will also at least contain the minimal essential sortase ligation motif, i.e., two glycine residues.

In one embodiment the conjugate as disclosed herein comprise bound to each other via a cystine bond two recombinant immunoglobulin heavy chain fragments comprising a VH-domain a CH1 domain a hinge region down to the last cysteine of the middle hinge region, two or more amino acids between the C-terminal most cysteine of the middle hinge region, the sequence LPXT (SEQ ID NO: 03, wherein X can be any amino acid residue) and at least two glycine residues.

In one embodiment the conjugate as disclosed herein will comprise bound to each other via a cystine bond two recombinant immunoglobulin heavy chain fragments, said heavy chain fragments comprising a VH-domain a CH1 domain a hinge region down to the last cysteine of the middle hinge region, two or more amino acids between the C-terminal most cysteine of the middle hinge region, the sequence LPXT (SEQ ID NO: 03, wherein X can be any amino acid residue) and at least two glycine residues; and two immunoglobulin light chains.

Conjugates comprising a label as reported herein may be useful in diagnostic assays, e.g., for detecting an antigen of interest in a whole blood, plasma or serum sample. The labeled conjugate as reported herein may be employed in any known assay method, such as ELISA, competitive binding assays, direct and indirect sandwich assays, and immunoprecipitation assays (Zola, Monoclonal Antibodies: A Manual of Techniques (1987) pp. 147-158, CRC Press, Inc.).

Labeled conjugates as reported herein alternatively will also be useful as imaging biomarkers and probes by the various methods and techniques of biomedical and molecular imaging such as: (i) MRI (magnetic resonance imaging); (ii) MicroCT (computerized tomography); (iii) SPECT (single photon emission computed tomography); (iv) PET (positron emission tomography) Tinianow, J. et al, Nuclear Medicine and Biology, 37(3) (2010) 289-297; Chen et al, Bioconjugate Chem. 15 (2004) 41-49; US 2010/0111856 (v) bioluminescence; (vi) fluorescence; and (vii) ultrasound. Immunoscintigraphy is an imaging procedure in which conjugates labeled with radioactive substances are administered to an animal or human patient and a picture is taken of sites in the body where the conjugate localizes (U.S. Pat. No. 6,528,624). Imaging biomarkers may be objectively measured and evaluated as an indicator of normal biological processes, pathogenic processes, or pharmacological responses to a therapeutic intervention.

The sortase nucleophile in one embodiment consists of the sortase ligation motif and the tag. In a further embodiment the sortase nucleophile consists of the sortase ligation motif a linker and the tag. The term "linker" herein denotes a bifunctional or multifunctional moiety which can has been used to conjugate (link) a first moiety with a second moiety. Linker-comprising sortase nucleophiles can be conveniently prepared using a linker having two reactive functionalities.

The linker may comprise amino acid residues which link the sortase ligation motif to the tag. The amino acid residues may form a dipeptide, tripeptide, tetrapeptide, pentapeptide, hexapeptide, heptapeptide, octapeptide, nonapeptide, decapeptide, undecapeptide or dodecapeptide unit. Amino acid residues include those occurring naturally, as well as non-naturally occurring amino acid analogs, such as e.g. citrulline or □□amino acids, such as e.g. β-alanine, or ω-amino acids such as 4-amino-butyric acid.

Typically, peptide-type linkers can be prepared by forming a peptide bond between two or more amino acids and/or peptide fragments. Such peptide bonds can be prepared, for example, according to the liquid phase synthesis method (E. Schroder and K. Lubke "The Peptides", volume 1 (1965) 76-136, Academic Press) which is well known in the field of peptide chemistry.

In another embodiment, the linker may comprise, consist of, or be substituted with groups which modulated solubility or reactivity. For example, a charged substituent such as sulfonate ($SO_3^-$) or ammonium in the linker may increase water solubility of the sortase nucleophile. A linker consisting of a polymer such as PEG may also exhibit positive effects, e.g. may lead to reduction of non-specific binding.

As shown in the below examples the F(ab')2-like conjugates produced with a method according to the present invention exhibit significant advantages as compared to F(ab')2-conjugates obtained by state-of-the-art procedures.

The following examples, figures and sequences are provided to aid the understanding of the present invention, the true scope of which is set forth in the appended claims. It is understood that modifications can be made in the procedures set forth without departing from the spirit of the invention.

Although the foregoing invention has been described in some detail by way of illustration and example for purposes of clarity of understanding, the descriptions and examples should not be construed as limiting the scope of the invention.

EXAMPLES

Recombinant DNA Techniques

Standard methods were used to manipulate DNA as described in Sambrook, J. et al., Molecular cloning: A laboratory manual; Cold Spring Harbor Laboratory Press, Cold Spring Harbor, N.Y., 1989. The molecular biological reagents were used according to the manufacturer's instructions.

Gene and Oligonucleotide Synthesis

Desired gene segments were prepared by chemical synthesis at Geneart GmbH (Regensburg, Germany). The synthesized gene fragments were cloned into an E. coli plasmid for propagation/amplification. The DNA sequences of subcloned gene fragments were verified by DNA sequencing. Alternatively, short synthetic DNA fragments were assembled by annealing chemically synthesized oligonucleotides or via PCR. The respective oligonucleotides were prepared by metabion GmbH (Planegg-Martinsried, Germany).

Description of the Basic/Standard Mammalian Expression Plasmid

For the expression of a desired gene/protein (e.g. full length antibody heavy chain, full length antibody light chain, or an Fc-chain containing an oligoglycine at its N-terminus) a transcription unit comprising the following functional elements is used:
- the immediate early enhancer and promoter from the human cytomegalovirus (P-CMV) including intron A,
- a human heavy chain immunoglobulin 5'-untranslated region (5'UTR),
- a murine immunoglobulin heavy chain signal sequence,
- a gene/protein to be expressed (e.g. full length antibody heavy chain), and
- the bovine growth hormone polyadenylation sequence (BGH pA).

Beside the expression unit/cassette including the desired gene to be expressed the basic/standard mammalian expression plasmid contains
- an origin of replication from the vector pUC18 which allows replication of this plasmid in E. coli, and
- a beta-lactamase gene which confers ampicillin resistance in E. coli.

Protein Determination

The protein concentration of purified polypeptides was determined by determining the optical density (OD) at 280 nm, using the molar extinction coefficient calculated on the basis of the amino acid sequence of the polypeptide.

Example 1

Generation of an Expression Plasmid for Soluble S. aureus Sortase A

The sortase gene encodes an N-terminally truncated Staphylococcus aureus sortase A (60-206) molecule (amino acid sequence of SEQ ID NO: 17).

The expression plasmid for the transient expression of soluble sortase in HEK293 cells comprised besides the soluble sortase expression cassette an origin of replication from the vector pUC18, which allows replication of this plasmid in E. coli, and a beta-lactamase gene which confers ampicillin resistance in E. coli.

The transcription unit of the soluble sortase comprised the following functional elements:
- the immediate early enhancer and promoter from the human cytomegalovirus (P-CMV) including intron A,
- a human heavy chain immunoglobulin 5'-untranslated region (5'UTR),
- a murine immunoglobulin heavy chain signal sequence,
- a purification tag encoding nucleic acid,
- an N-terminally truncated S. aureus sortase A encoding nucleic acid, and
- the bovine growth hormone polyadenylation sequence (BGH pA).

The amino acid sequence of the mature soluble sortase is (SEQ ID NO: 17)
QAKPQIPKDKSKVAGYIEIPDADIKEPVYPGPATPEQLNRGVSFAEENESL

DDQNISIAGHTFIDRPNYQFTNLKAAKKGSMVYFKVGNETRKYKMTSIRDV

KPTDVGVLDEQKGKDKQLTLITCDDYNEKTGVWEKRKIFVATEVK.

The purification tag has the amino acid sequence MRGSHHHHHHGS (SEQ ID NO: 18).

Example 2

Transient Expression and Analytical Characterization of Recombinant Immunoglobulin Heavy Chains Comprising a Sortase Conjugation Loop The recombinant production was performed by transient transfection of HEK293 cells (human embryonic kidney cell line 293-derived) cultivated in F17 Medium (Invitrogen Corp.). For transfection "293-Fectin" Transfection Reagent (Invitrogen) was used. Transfection was performed as specified in the manufacturer's instructions. Cell culture supernatants were harvested three to seven (3-7) days after transfection. Supernatants were stored at reduced temperature (e.g. −80° C.).

General information regarding the recombinant expression of human immunoglobulins in e.g. HEK293 cells is given in: Meissner, P. et al., Biotechnol. Bioeng. 75 (2001) 197-203.

The recombinant immunoglobulin heavy chains of a M-IgG1 subclass comprising a sortase conjugation loop has been purified by caturing on a ProteinA Sepharose chromatographic bed material (e.g. MabSelect Sure, GE Healtcare) at slightly basic conditions (e.g. pH 8,0). The IgG has been eluted from the bed material using a citric acid buffer (100 mM, pH 4.0) and finally purified in a polishing step on a GPC column (e.g. Superdex 200 Increase, GE Healtcare) under appropriate chromatographic conditions (e.g. 100 mM phosphate buffer, pH 7.4).

The protein concentration of a purified polypeptide was determined by measuring the optical density (OD) at 280 nm, using the molar extinction coefficient calculated on the basis of the amino acid sequence. Purity was analyzed by GPC chromatography as well as SDS-PAGE in the presence and absence of a reducing agent (5 mM 1,4-dithiotreitol) and staining with Coomassie brilliant blue.

The identity of expressed recombinant immunoglobulin heavy chains comprising a sortase conjugation loop was confirmed by ESI TOF MS in term of comparison of theoretical and experimentally determined molecular weight of both light and heavy chain of recombinant immunoglobulin.

Example 3

Synthesis and Production of Vectors for Recombinant Immunoglobulin

Standard methods were used to manipulate DNA as described in Sambrook, J. et al., Molecular cloning: A laboratory manual; Cold Spring Harbor Laboratory Press, Cold Spring Harbor, N.Y., 1989. The molecular biological reagents were used according to the manufacturer's instructions.

In details, desired gene segments of both light and heavy chains of recombinant immunoglobulin comprising the sequence encoding for a sortase conjugation loop were generated by conventional PCR-based cloning techniques. Therefore, the cDNA of the genes encoding the light and the heavy of the desired antibody was amplified with gene-specific oligonucleotides/primers containing restriction sites for molecular cloning. Sequence encoding for a sortase conjugation loops were introduced in two step PCR-strategy using sortase conjugation loop containing primers in combination with gene-specific primers. The respective oligonucleotides were prepared by metabion GmbH (Planegg-Martinsried, Germany) or ThermoFisher.

Alternatively, the desired gene segments of both light and heavy chains of recombinant immunoglobulin comprising the sequence encoding for a sortase conjugation loop were either prepared by chemical synthesis at GeneArt® ThermoFisher.

The synthesized gene fragments were cloned into an *E. coli* shuttle vector for propagation/amplification in *E. coli* and transient expression in HEK293 cells. The DNA sequences of subcloned gene fragments were verified by DNA sequencing.

For the expression of a desired gene/protein (e.g. full length antibody heavy chain comprising a sortase conjugation loop, full length antibody light chain) a transcription unit comprising the following functional elements is used:
 the immediate early enhancer and promoter from the human cytomegalovirus (P-CMV)
 an immunoglobulin heavy chain signal sequence including an intron
 a gene/protein to be expressed (comprising a sortase conjugation loop, full length antibody light chain), and
 the bovine growth hormone polyadenylation sequence (BGH pA).

Beside the expression unit/cassette including the desired gene to be expressed the basic/standard mammalian expression plasmid contains
 an origin of replication from the vector pUC18 which allows replication of this plasmid in *E. coli*, and
 a beta-lactamase gene which confers ampicillin resistance in *E. coli*.

Example 4

Sortase-Mediated Fusion of Glucose Dehydrogenase and Biotinylated Oligo-Glycin

With the method as outlined below the activity of a sortase-mediated enzymatic conjugation/coupling reaction can be determined photometricly by fusing a glucose dehydrogenase as reporter enzyme to a sortase amino acid motif (LPETG (SEQ ID NO:24) or LPETA (SEQ ID NO:25)) and using this as first substrate. As second substrate biotinylated oligo-glycin or oligo-alanine is used (nucleophile). When the sortase is added to a solution containing the first and the second substrate a conjugate is formed by sortase-mediated conjugation of the first and the second substrate which is a biotinylated reporter enzyme. The biotinylated reporter enzyme can be recovered using a streptavidin-coated magnetic beads. When a substrate for the reporter enzyme is added, the product can be detected by the change of optical density.

Purified sortase was mixed with its substrates, i.e. a glucose dehydrogenase containing the LPETG (SEQ ID NO:24) or LPETA (SEQ ID NO:25) motif (20 µM) and a biotin derivative containing N-terminal glycines or alanines (330 µM) in 50 mM Tris buffer pH 7.5 containing 200 mM NaCl. The reaction mixture was incubated at 37° C. for two hours. The reaction was stopped by addition of a 10- to 20-fold excess of inhibition buffer (50 mM Tris, pH 7.5, 200 mM NaCl, 10 mM $CaCl_2$, 5 mM iodoacetamide). The stopped reaction mixture was centrifuged for 10 min. at 5000×g. The supernatant (50 µL) was added to 100 µL of 50 mM Tris buffer (pH 7.5) comprising 200 mM NaCl, 10 mM $CaCl_2$) and streptavidin coted magnetic beads were added and incubated for 30 min. at 30° C. at 200 rpm. Thereafter the magnetic beads were washed five times with 300 µL washing buffer each (50 mM Tris, pH 7.5, 200 mM NaCl, 10 mM $CaCl_2$, 5 mg/mL BSA, 0.1% Triton X-100) in V-bottom multi-well plates using a magnet and a vacuum pump. Afterwards the beads are resuspended in 100 µL citrate test buffer and 10-80 µL thereof were transferred to a new well. Thereto 150 µL test buffer (0.2 M sodium citrate, pH 5.8, 0.3 g/L 4-nitrosoanilin, 1 mM $CaCl_2$, 30 mM glucose) was added.

The kinetic of the reporter enzyme is measured over a time period of 5 min. at 620 nm. The activity of the reporter enzyme is proportional to the amount of immobilized enzyme, which is proportional to the amount of biotinylated enzyme and this is proportional to the activity of the sortase.

Example 5

Figure 2:
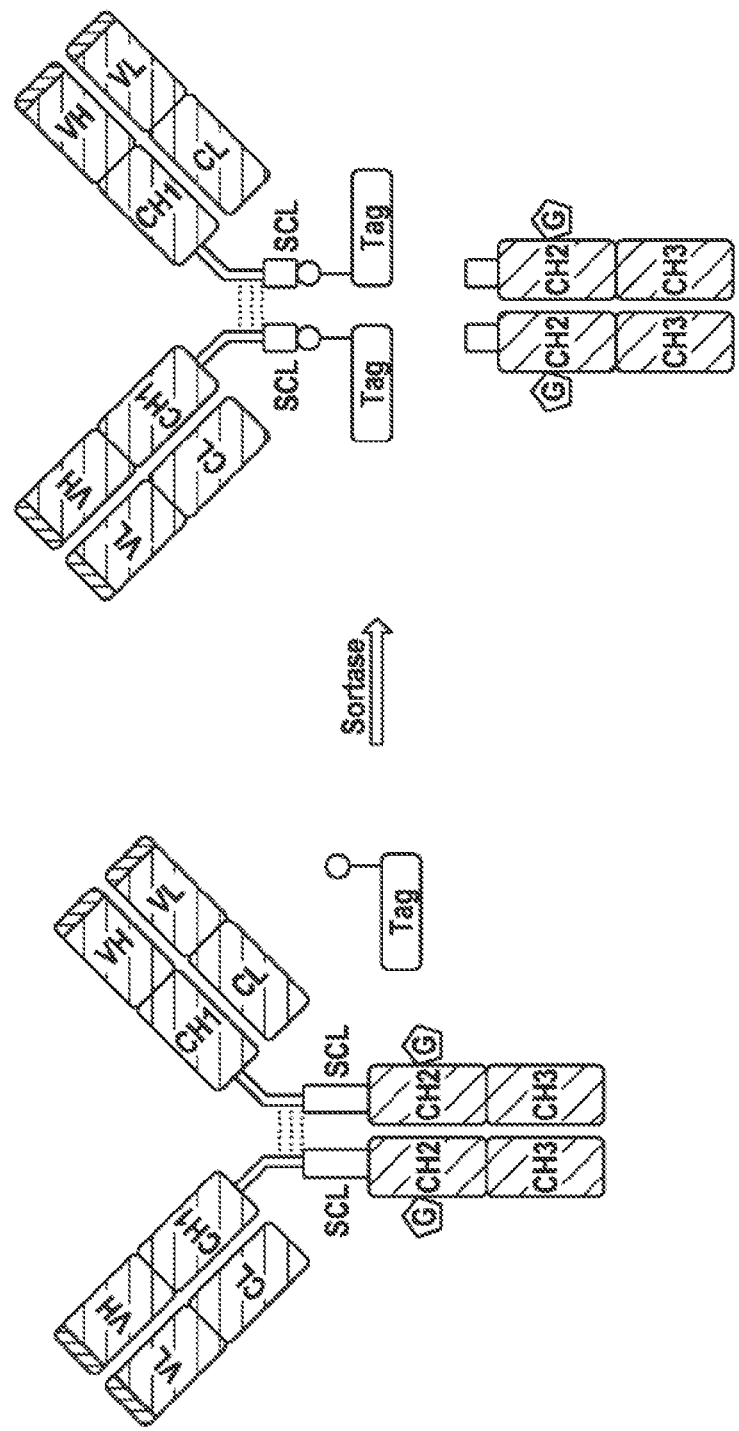
FIG. 2 Scheme of a sortase mediated one-step cleavage and conjugation protocol. The symbols shown are as follows:
VL, VH, CL, CH1, CH2, CH3=common domains of an IgG
G=glycosylation
SCL=sortase conjugation loop
Tag=sortase tag with nuclophile FIG. 3 Structure of sortase nucleophile comprising a GGGG (SEQ ID NO:23) ligation motif and biotin tag.

Sortase-Mediated Fusion of Recombinant Immunoglobulin Comprising a Sortase Conjugation Loop With the method as outlined below an enzymatic cleavage of an IgG comprising a sortase conjugation loop (substrate 1) and a subsequent conjugation/coupling reaction of a biotin tag (substrate 2). When the sortase is added to a solution containing the first and the second substrate, a C-terminally biotinylated F(ab')2 fragment is formed by sortase-mediated conjugation of the first and the second substrate (see FIG. 2).

The amino acid sequence of sortase conjugation loop in the heavy chain of a IgG immunoglobulin is designed according to standard procedures. An exemplary sequence of a mouse immunoglobulin G1 heavy chain was as follows:
 (VH domain)-(CH1 domain)-(hinge region with inserted sortase conjugation loop=VPRDCGCKPCICTGSGSGG-VLPETGVGSGSGGAGSGSS) (SEQ ID NO: 19)-(CH2 domain)-(CH3 domain)

Wherein the sequence 19 (SEQ ID NO: 19) comprises the following parts:
 VPRDCGCKPCICT (SEQ ID NO: 20)=upper and middle hinge region and the sortase conjugation loop GSGSGGVL-PETGVGSGSGGAGSGSS (SEQ ID NO: 21).

Figure 3:
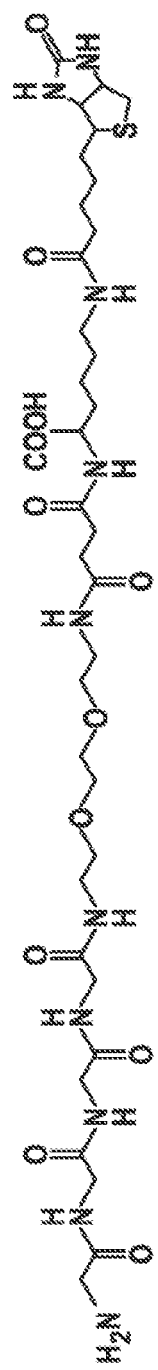

The structure of sortase nucleophile comprising of ligation motif (GGGG) (SEQ ID NO:23) and the tag (biotin) can be designed as required. (An example of such structure is given in FIG. 3).

Purified sortase (20 µM) was mixed with its substrates, i.e. recombinant immunoglobulin comprising a sortase conjugation loop (30 µM) and a biotin derivative containing N-terminal GGGG (SEQ ID NO:23) nucleophile motif (1500 µM) in 50 mM Tris buffer pH 8.0 containing 150 mM KCl and 5 mM $CaCl_2$. The reaction mixture was incubated at 37° C. for 17 hours (overnight). The reaction was stopped by addition of 0.5 M EDTA, pH 7.5 ad 5 mM in the reaction mixture.

Figure 4:
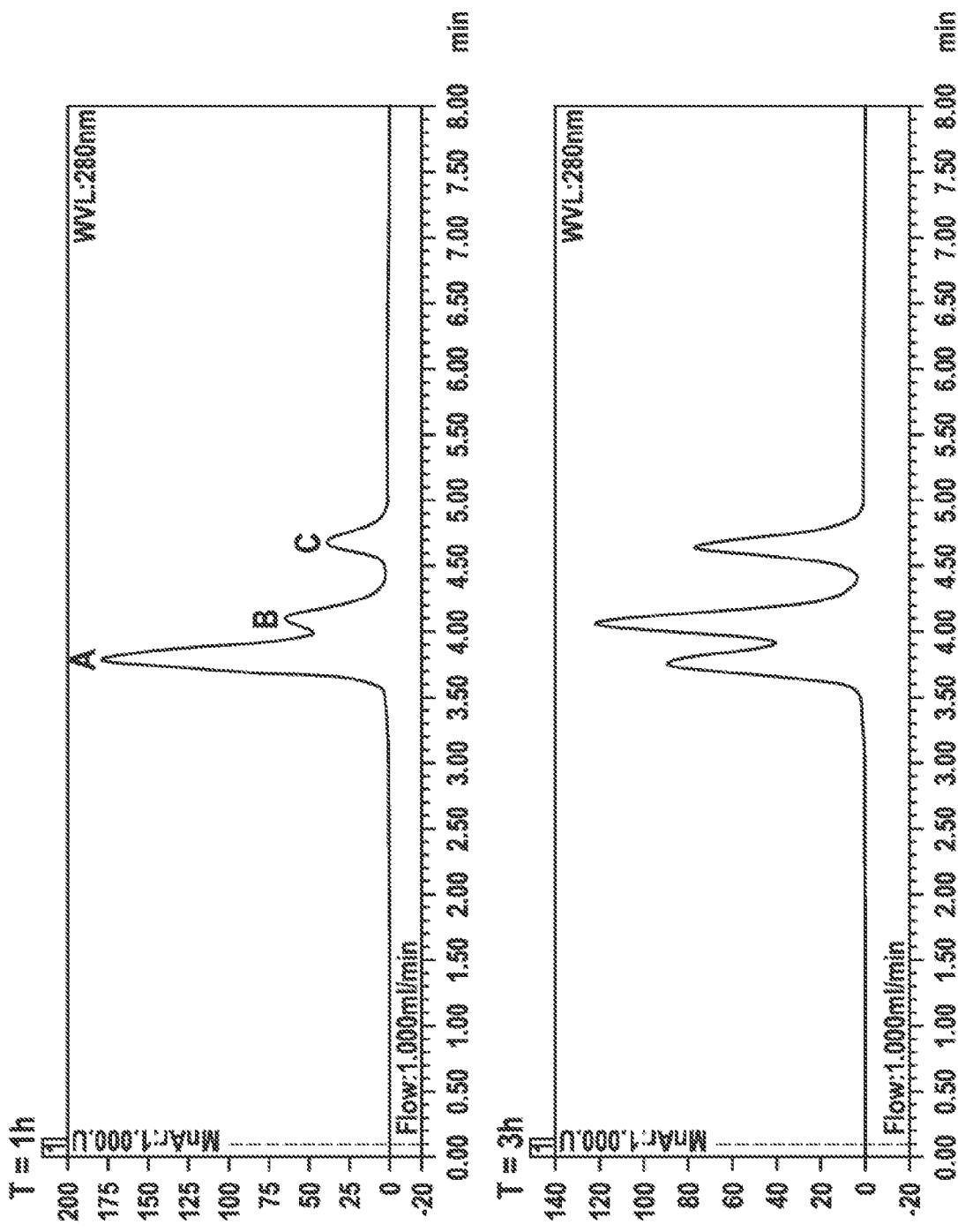
FIG. 4 Monitoring of the sortase-mediated cleavage; Selected chromatograms obtained by GPC monitoring of the cleavage reaction taken at 1 h, 3 h, 10 h and 15 h, respectively, after start of the reaction.
(A) IgG; (B) C-terminally biotinylated F(ab')2 fragment; (C) Fc☐ fragment FIG. 5 Results of the comparative evaluation of a state of the art conjugate and a conjugate according to the present disclosure; Shown are the ECL-signals for a biotin-NHS labeled enzymatically (papain) cleaved F(ab')2 fragment (A) and a sortase cleaved/biotin-conjugated F(ab')2 fragment (B).

The progress of cleavage reaction was monitored by GPC chromatography (GFC300 Tosoh; 100 mM phosphate buffer, pH 7.0; 1 ml/min; detection at 280 nm) as well as SDS PAGE. The residual amount of full IgG decreased below 5% within 6 hours after addition of sortase into the reaction mixture and below 3.6% within 15 hours, respectively (see FIG. 4).

The cleaved and biotin-conjugated F(ab')2 fragment was purified using a ProteinA Sepharose chromatographic bed material (e.g. MabSelect Sure, GE Healtcare) at slightly basic conditions (e.g. pH 8,0). The residual IgG as well as Fc part has been captured on the bed material. The flow-through fraction of a biotinylated F(ab')2 has been concentrated by an ultrafiltration membrane (15 MWCO, Amicon-Ultra) and finally purified in a polishing step on a GPC column (e.g. Superdex 200 Increase, GE Healtcare) under appropriate chromatographic conditions (e.g. 50 mM phosphate buffer, 150 mM KCl, pH 7.4).

The identity of cleaved/conjugated recombinant immunoglobulin comprising a sortase conjugation loop to a biotinylated F(ab')2 was confirmed by ESI TOF MS in term of comparison of theoretical and experimentally determined molecular weight. The biotin incorporation rate is exactly 2 (each heavy chain is in a cleaved and C-terminally biotinylated form). The yield of cleavage/conjugation/purification procedure was appr. 33% (maximal theoretical yield is appr. 60%)—compare with the yield of a NHS-conjugated mono-biotinylated F(ab')2 fragment of appr. 10-15%. The functional testing is described in the Examples 7 and 8, respectively.

Example 6

Sortase-Mediated Fusion of Recombinant Rabbit Immunoglobulin Comprising a Sortase Conjugation Loop With the method as outlined in the Example 5, an enzymatic cleavage of a rabbit/mouse IgG chimera, clone B comprising a sortase conjugation loop (substrate 1) and a subsequent conjugation/coupling reaction of a biotin tag (substrate 2) was tested.

The amino acid sequence of sortase conjugation loop in the heavy chain of a IgG immunoglobulin is designed essentially as described in the Example 5.

Purified sortase (40 µM) was mixed with its substrates, i.e. recombinant immunoglobulin comprising a sortase conjugation loop (60 µM) and a biotin derivative containing N-terminal GGGG (SEQ ID NO:23) nucleophile motif (3000 µM) in 50 mM Tris buffer pH 8.0 containing 150 mM KCl and 5 mM $CaCl_2$. The reaction mixture was incubated at 37° C. for 17 hours (overnight). The reaction was stopped by addition of 0.5 M EDTA, pH 7.5 ad 5 mM in the reaction mixture.

The progress of cleavage reaction was monitored by GPC chromatography (GFC300 Tosoh; 100 mM phosphate buffer, pH 7.0; 1 ml/min; detection at 280 nm) as well as by SDS PAGE. The residual amount of full-length, i.e non-sortase-cleaved IgG decreased below 10% within 15 hours. The F(ab')2 product was fully biotinylated with the biotin incorporation rate of 2 (data not shown).

Example 7

Immunoassay Data Using a Conventional F(Ab')2-Fragment and a F(Ab')2-Like Fragment as Produced in Example 5

The biotinylated F(ab')2 conjugated prepared according to the presented sortase mediated protocol (see Example 5) was compared with a NHS-conjugated mono-biotinylated pepsin prepared F(ab')2 fragment of the same monoclonal antibody.

In the first case, the biotin is site directed attached to the C-terminus of heavy chains consisting of sortase conjugation loop providing a defined homogenous population of conjugated fragments (see Example 5).

In the second case, the biotin is attached stochastically on different lysines of a F(ab')2 fragment according to standard protocols. In order to obtain mono-biotinylated antibody conjugates 0.5-1 M ammonium sulfate was added to the conjugate solution. The solution was passed through a streptavidin mutein adsorber (see DE19637718) equilibrated with 50 mM potassium phosphate (pH 7.5), 150 mM KCl, 0.5-1 M ammonium sulfate. Antibodies without any biotin coupled/bound to them are unable to bind the adsorber and were washed out. Mono-biotinylated antibody conjugates were eluted with 50 mM potassium phosphate (pH 7.5), 150 mM KCl and 2% DMSO. Antibody conjugates with more than one biotin per antibody were eluted thereafter with 50 mM potassium phosphate (pH 7.5), 150 mM KCl and 2 mM biotin. The mono-biotinylated fraction obtained comprises a heterogeneous population of different mono-biotinylated F(ab')2 fragments.

The comparative evaluation was performed using an experimental TSH electrochemiluminescense assay. Measurements were carried out in a sandwich assay format on a Cobas® e411 analyzer from Roche. Signal detection in the Cobas® e411 analyzer is based on electrochemiluminescense. In this sandwich assay the biotin-conjugate (i.e. the capture antibody) is immobilized on the surface of a streptavidin-coated magnetic bead. The detection-antibody bears a complexed ruthenium cation as the signaling moiety. In the presence of analyte, the chromogenic ruthenium complex is bridged to the solid phase and emits light at 620 nm after excitation at the platinum electrode comprised in the measuring cell of the Cobas® e601 analyzer. The signal output is in arbitrary light units. Measurements were performed with calibrators spiked with TSH as well as human serum samples purchased from several sources.

The experimental TSH assay was conducted as follows. 50 µl of human serum sample or of spiked calibrator, 35 µl of 2 µg/ml capture antibody-biotin conjugate and 50 µl of 1 µg/ml detection antibody ruthenium label conjugate were incubated together for 9 minutes followed by the addition of 40 µl streptavidin-coated paramagnetic microparticles. The mixture was incubated for further 9 minutes. Afterwards, the TSH was detected (via the electrochemiluminescent signal generated in these experiments).

Results or calibrators obtained in an experimental TSH Elecsys are sumarized in the table below. The results demonstrate that a C-terminally site directed biotinylation of a F(ab')2 fragment is beneficious over a mono-biotinylated F(ab')2 fragment conjugated stochastically through free lysines. The assay dynamics increased from 92 to 145 for calibrator 6, and from 6.8 to 10.2 for the calibrator 2, respectively (see FIG. 5). The blank values remained unaffected.

| μU/mL of TSH | | NHS-labeled F(ab')2 conjugate (A) [counts] | sortase labeled F(ab')2 conjugate (B) [counts] |
|---|---|---|---|
| Cal1 | 0 | 709 | 693 |
| Cal2 | 0.31 | 4877 | 7039 |
| Cal3 | 0.63 | 9211 | 13471 |
| Cal4 | 1.25 | 17356 | 25919 |
| Cal5 | 2.5 | 33166 | 50123 |
| Cal6 | 5 | 65469 | 100544 |

Example 8

Immunoassay Data Using a F(Ab')2-Fragment as Produced in Example 5 and a Conventional IgG Conjugate The biotinylated F(ab')2 conjugated prepared according to the presented sortase mediated protocol (see Example 5) was compared with a NHS-conjugated mono-biotinylated IgG of the same monoclonal antibody.

In the first case, the biotin is site directed attached to the C-terminus of heavy chains consisting of sortase conjugation loop providing a defined homogenous population of conjugated fragments (see Example 5).

In the second case, the biotin is attached stochastically on different lysines of an IgG according to standard protocols. In order to obtain mono-biotinylated antibody, a procedure for the preparation of a conventional conjugate described in the Example 6 has been applied.

The comparative evaluation was performed using an experimental pTau electrochemiluminescense assay. Measurements were carried out in a sandwich assay format on a Cobas® e601 analyzer from Roche. Signal detection in the Cobas® e601 analyzer is based on electrochemiluminescense. The technical realization of a sandwich assay is described in the Example 6.

The experimental phospho-Tau(181P) assay was conducted as follows. 55 μl of human serum sample or of spiked calibrator, 50 μl of 1 μg/ml capture antibody-biotin conjugate and 60 μl of 2 μg/ml detection antibody ruthenium label conjugate were incubated together for 9 minutes followed by the addition of 35 μl streptavidin-coated paramagnetic microparticles. The mixture was incubated for further 9 minutes. Afterwards, the phosphor-Tau was detected (via the electrochemiluminescent signal generated in these experiments).

Figure 6:
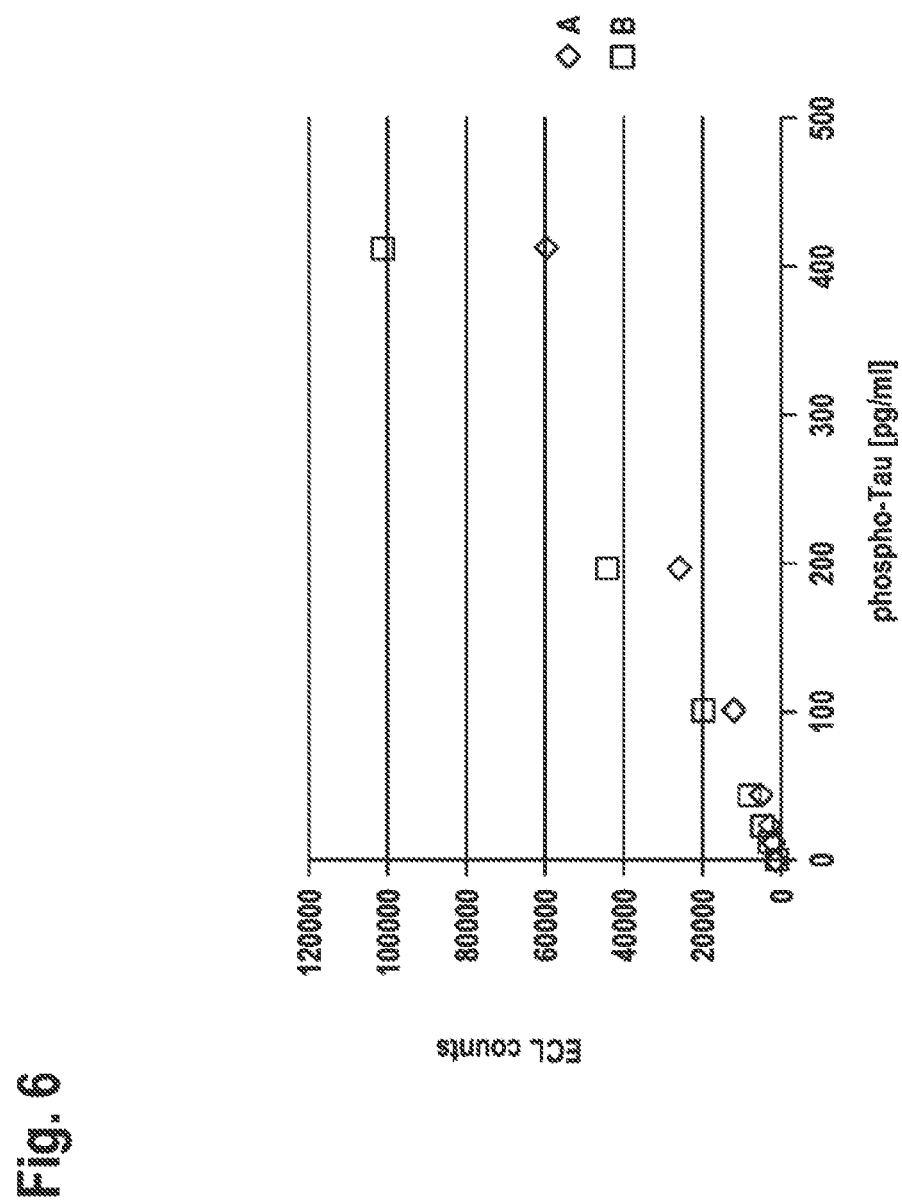
FIG. 6 Results of the comparative evaluation of a state of the art conjugate and a conjugate according to the present disclosure; Shown are the ECL-signals for a biotin-NHS labeled IgG (A) and a sortase cleaved/biotin-conjugated F(ab')2 fragment (B).

Results for calibrators obtained in an experimental phospho-Tau Elecsys are sumarized in the table below. The results demonstrate that a C-terminally site directed biotinylation of a F(ab')2 fragment is beneficious over a mono-biotinylated IgG conjugated stochastically through free lysines. The assay dynamics increased from 57 to 86 for calibrator 7, and from 3.0 to 4.1 for the calibrator 3, respectively (see FIG. 6). The blank values remained unaffected.

| | pg/mL of phospho-Tau | NHS-labeled IgG conjugate (A) [counts] | sortase labeled F(ab')2 conjugate (B) [counts] |
|---|---|---|---|
| Cal1 | 0 | 1060 | 1180 |
| Cal2 | 12.12 | 2140 | 2982 |
| Cal3 | 23.56 | 3189 | 4843 |
| Cal4 | 44.65 | 5520 | 8428 |
| Cal5 | 103 | 12493 | 20455 |
| Cal6 | 200.7 | 26372 | 44394 |
| Cal7 | 420.6 | 60086 | 101898 |

The invention claimed is:

1. A recombinant immunoglobulin heavy chain comprising a VH-domain, a CH1 domain, a hinge region down to the C-terminal most cysteine of the middle hinge region, a sortase conjugation loop, a CH2 domain and a CH3 domain, wherein the sortase conjugation loop comprises:
   a) at least 16 amino acids located between the C-terminal most cysteine of the middle hinge region and the VFX1FPP (SEQ ID NO: 2; wherein X1 is L or I) consensus sequence at the N-terminus of an immunoglobulin heavy chain CH2-domain,
   b) a sortase recognition motif of the amino acid sequence LPX1TX2 (SEQ ID NO: 01), wherein X1 can be any amino acid residue and X2 is G or A,
   c) N-terminal to the sequence of (b) at least two amino acids, and
   d) C-terminal to the sequence of (b) at least 6 amino acids, and
   wherein the amino acids C- and N-terminal to the sequence of (b) are not cysteine.

2. The recombinant immunoglobulin heavy chain of claim 1, wherein said sortase conjugation loop comprises at least 9 amino acids C-terminal to the sequence LPX1TX2 (SEQ ID NO: 01, wherein X1 can be any amino acid residue and X2 is G or A).

3. The recombinant immunoglobulin heavy chain of claim 1, wherein said sortase conjugation loop comprises at least 5 amino acids N-terminal to the sequence LPX1TX2 (SEQ ID NO: 01, wherein X1 can be any amino acid residue and X2 is G or A).

4. The recombinant immunoglobulin heavy chain of claim 1, wherein said sortase conjugation loop comprises at least 8 amino acids N-terminal to the sequence LPX1TX2 (SEQ ID NO: 01, wherein X1 can be any amino acid residue and X2 is G or A).

5. The recombinant immunoglobulin heavy chain according to claim 1, wherein said sortase conjugation loop comprises at least 5 amino acids N-terminal to the sequence LPX1TX2 (SEQ ID NO: 01, wherein X1 can be any amino acid residue and X2 is G or A), and at least 9 amino acids C-terminal to said sequence.

6. The recombinant immunoglobulin heavy chain according to claim 1, wherein said sortase conjugation loop comprises at least 8 amino acids N-terminal to the sequence LPX1TX2 (SEQ ID NO: 01, wherein X1 can be any amino acid residue and X2 is G or A), and at least 9 amino acids C-terminal to said sequence.

7. The recombinant immunoglobulin heavy chain according to claim 1, wherein said sortase conjugation loop is at most 50 amino acids long.

8. An antibody comprising at least two recombinant immunoglobulin heavy chains according to claim 1.

9. An IgG class antibody having two recombinant immunoglobulin heavy chains according to claim 1.

10. A method for producing a conjugate of a sortase cleavage fragment of a recombinant immunoglobulin heavy chain and a sortase nucleophile comprising incubating
   i) the antibody according to claim 7,
   ii) a compound comprising a sortase nucleophile, and
   iii) a polypeptide with sortase activity, thereby cleaving the recombinant antibody heavy chain after the threonine in LPX1TX2 (SEQ ID NO: 01, wherein X1 can be any amino acid residue and X2 is G or A) and conjugating the N-terminus of the sortase nucleophile to said threonine.

11. The method according to claim 10, wherein the sortase nucleophile comprises a tag of interest and has the formula $(Gly)_n$-tag, wherein n is at least 2.

12. The method according to claim 10, wherein the sortase nucleophile comprises a tag of interest and has the formula $(Gly)_n$-tag and wherein n is selected from 2, 3, 4, 5 or 6.

13. The method according to claim 10, wherein the sortase nucleophile comprises a tag of interest and has the formula $(Gly)_n$-tag, wherein n is at most 30.

* * * * *

SEQUENCE LISTING

```
<160> NUMBER OF SEQ ID NOS: 49

<210> SEQ ID NO 1
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: X is any amino acid, selected independently
      from X at position 5
<220> FEATURE:
<221> NAME/KEY: MISC_FEATURE
<222> LOCATION: (5)..(5)
<223> OTHER INFORMATION: X is an amino acid selected from A and G,
      selected independently from X at position 3

<400> SEQUENCE: 1

Leu Pro Xaa Thr Xaa
1               5

<210> SEQ ID NO 2
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: X is any amino acid
```

```
<400> SEQUENCE: 2

Val Phe Xaa Phe Pro Pro
1               5

<210> SEQ ID NO 3
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: X is any amino acid

<400> SEQUENCE: 3

Leu Pro Xaa Thr
1

<210> SEQ ID NO 4
<211> LENGTH: 35
<212> TYPE: PRT
<213> ORGANISM: Homo sapiens

<400> SEQUENCE: 4

Thr Lys Val Asp Lys Lys Val Glu Pro Lys Ser Cys Asp Lys Thr His
1               5                   10                  15

Thr Cys Pro Pro Cys Pro Ala Pro Glu Leu Leu Gly Gly Pro Ser Val
            20                  25                  30

Phe Leu Phe
        35

<210> SEQ ID NO 5
<211> LENGTH: 31
<212> TYPE: PRT
<213> ORGANISM: Homo sapiens

<400> SEQUENCE: 5

Thr Lys Val Asp Lys Lys Val Glu Arg Lys Cys Cys Val Glu Cys Pro
1               5                   10                  15

Pro Cys Pro Ala Pro Pro Val Ala Gly Pro Ser Val Phe Leu Phe
            20                  25                  30

<210> SEQ ID NO 6
<211> LENGTH: 32
<212> TYPE: PRT
<213> ORGANISM: Homo sapiens

<400> SEQUENCE: 6

Thr Lys Val Asp Lys Arg Val Glu Ser Lys Tyr Gly Pro Pro Cys Pro
1               5                   10                  15

Ser Cys Pro Ala Pro Glu Phe Leu Gly Gly Pro Ser Val Phe Leu Phe
            20                  25                  30

<210> SEQ ID NO 7
<211> LENGTH: 30
<212> TYPE: PRT
<213> ORGANISM: Mus musculus
```

```
<400> SEQUENCE: 7

Thr Lys Val Asp Lys Ile Val Pro Arg Asp Cys Gly Cys Lys Pro
1               5                   10                  15

Cys Ile Cys Thr Val Pro Glu Val Ser Ser Val Phe Ile Phe
            20                  25                  30

<210> SEQ ID NO 8
<211> LENGTH: 36
<212> TYPE: PRT
<213> ORGANISM: Mus musculus

<400> SEQUENCE: 8

Thr Lys Val Asp Lys Ile Glu Pro Arg Gly Pro Thr Ile Lys Pro
1               5                   10                  15

Cys Pro Pro Cys Lys Cys Pro Ala Pro Asn Leu Leu Gly Gly Pro Ser
            20                  25                  30

Val Phe Ile Phe
        35

<210> SEQ ID NO 9
<211> LENGTH: 41
<212> TYPE: PRT
<213> ORGANISM: Mus musculus

<400> SEQUENCE: 9

Thr Lys Val Asp Lys Lys Ile Glu Pro Arg Val Pro Ile Thr Gln Asn
1               5                   10                  15

Pro Cys Pro Pro Leu Lys Glu Cys Pro Pro Cys Ala Ala Pro Asp Leu
            20                  25                  30

Leu Gly Gly Pro Ser Val Phe Ile Phe
            35                  40

<210> SEQ ID NO 10
<211> LENGTH: 42
<212> TYPE: PRT
<213> ORGANISM: Mus musculus

<400> SEQUENCE: 10

Thr Thr Val Asp Lys Lys Leu Glu Pro Ser Gly Pro Ile Ser Thr Ile
1               5                   10                  15

Asn Pro Cys Pro Pro Cys Lys Glu Cys His Lys Cys Pro Ala Pro Asn
            20                  25                  30

Leu Glu Gly Gly Pro Ser Val Phe Ile Phe
            35                  40

<210> SEQ ID NO 11
<211> LENGTH: 36
<212> TYPE: PRT
<213> ORGANISM: Mus musculus

<400> SEQUENCE: 11

Thr Glu Leu Ile Lys Arg Ile Glu Pro Arg Ile Pro Lys Pro Ser Thr
1               5                   10                  15

Pro Pro Gly Ser Ser Cys Pro Ala Gly Asn Ile Leu Gly Gly Pro Ser
            20                  25                  30

Val Phe Ile Phe
        35
```

<210> SEQ ID NO 12
<211> LENGTH: 31
<212> TYPE: PRT
<213> ORGANISM: Oryctolagus cuniculus

<400> SEQUENCE: 12

Thr Lys Val Asp Lys Thr Val Ala Pro Ser Thr Cys Ser Lys Pro Thr
1               5                   10                  15

Cys Pro Pro Pro Glu Leu Leu Gly Gly Pro Ser Val Phe Ile Phe
            20                  25                  30

<210> SEQ ID NO 13
<211> LENGTH: 34
<212> TYPE: PRT
<213> ORGANISM: Ovis aries

<400> SEQUENCE: 13

Thr Lys Val Asp Lys Arg Val Glu Pro Gly Cys Pro Asp Pro Cys Lys
1               5                   10                  15

His Cys Arg Cys Pro Pro Pro Glu Leu Pro Gly Gly Pro Ser Val Phe
            20                  25                  30

Ile Phe

<210> SEQ ID NO 14
<211> LENGTH: 7
<212> TYPE: PRT
<213> ORGANISM: Homo sapiens

<400> SEQUENCE: 14

Thr Lys Val Asp Lys Arg Val
1               5

<210> SEQ ID NO 15
<211> LENGTH: 62
<212> TYPE: PRT
<213> ORGANISM: Homo sapiens

<400> SEQUENCE: 15

Glu Leu Lys Thr Pro Leu Gly Asp Thr Thr His Thr Cys Pro Arg Cys
1               5                   10                  15

Pro Glu Pro Lys Ser Cys Asp Thr Pro Pro Pro Cys Pro Arg Pro Cys
            20                  25                  30

Glu Pro Lys Ser Cys Asp Thr Pro Pro Pro Cys Pro Arg Pro Cys Glu
        35                  40                  45

Pro Lys Ser Cys Asp Thr Pro Pro Pro Cys Pro Arg Pro Cys
    50                  55                  60

<210> SEQ ID NO 16
<211> LENGTH: 13
<212> TYPE: PRT
<213> ORGANISM: Homo sapiens

<400> SEQUENCE: 16

Ala Pro Glu Leu Leu Gly Gly Pro Ser Val Phe Leu Phe
1               5                   10

<210> SEQ ID NO 17
<211> LENGTH: 147
<212> TYPE: PRT
<213> ORGANISM: Staphylococcus aureus

<400> SEQUENCE: 17

Gln Ala Lys Pro Gln Ile Pro Lys Asp Lys Ser Lys Val Ala Gly Tyr
1               5                   10                  15

Ile Glu Ile Pro Asp Ala Asp Ile Lys Glu Pro Val Tyr Pro Gly Pro
                20                  25                  30

Ala Thr Pro Glu Gln Leu Asn Arg Gly Val Ser Phe Ala Glu Glu Asn
            35                  40                  45

Glu Ser Leu Asp Asp Gln Asn Ile Ser Ile Ala Gly His Thr Phe Ile
        50                  55                  60

Asp Arg Pro Asn Tyr Gln Phe Thr Asn Leu Lys Ala Lys Lys Gly
65                  70                  75                  80

Ser Met Val Tyr Phe Lys Val Gly Asn Glu Thr Arg Lys Tyr Lys Met
                85                  90                  95

Thr Ser Ile Arg Asp Val Lys Pro Thr Asp Val Gly Val Leu Asp Glu
            100                 105                 110

Gln Lys Gly Lys Asp Lys Gln Leu Thr Leu Ile Thr Cys Asp Asp Tyr
        115                 120                 125

Asn Glu Lys Thr Gly Val Trp Glu Lys Arg Lys Ile Phe Val Ala Thr
130                 135                 140

Glu Val Lys
145

<210> SEQ ID NO 18
<211> LENGTH: 12
<212> TYPE: PRT
<213> ORGANISM: Artificial Sequence
<220> FEATURE:
<223> OTHER INFORMATION: Synthetic

<400> SEQUENCE: 18

Met Arg Gly Ser His His His His His His Gly Ser
1               5                   10

<210> SEQ ID NO 19
<211> LENGTH: 38
<212> TYPE: PRT
<213> ORGANISM: Artificial Sequence
<220> FEATURE:
<223> OTHER INFORMATION: Synthetic

<400> SEQUENCE: 19

Val Pro Arg Asp Cys Gly Cys Lys Pro Cys Ile Cys Thr Gly Ser Gly
1               5                   10                  15

Ser Gly Gly Val Leu Pro Glu Thr Gly Val Gly Ser Gly Ser Gly Gly
            20                  25                  30

Ala Gly Ser Gly Ser Ser
        35

<210> SEQ ID NO 20
<211> LENGTH: 13
<212> TYPE: PRT
<213> ORGANISM: Mus musculus

<400> SEQUENCE: 20

Val Pro Arg Asp Cys Gly Cys Lys Pro Cys Ile Cys Thr
1               5                   10

```
<210> SEQ ID NO 21
<211> LENGTH: 25
<212> TYPE: PRT
<213> ORGANISM: Artificial Sequence
<220> FEATURE:
<223> OTHER INFORMATION: Synthetic

<400> SEQUENCE: 21

Gly Ser Gly Ser Gly Gly Val Leu Pro Glu Thr Gly Val Gly Ser Gly
1               5                   10                  15

Ser Gly Gly Ala Gly Ser Gly Ser Ser
            20                  25

<210> SEQ ID NO 22
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa can be any naturally occurring amino acid

<400> SEQUENCE: 22

Leu Pro Xaa Thr Gly
1               5

<210> SEQ ID NO 23
<211> LENGTH: 4
<212> TYPE: PRT
<213> ORGANISM: Artificial Sequence
<220> FEATURE:
<223> OTHER INFORMATION: Synthetic

<400> SEQUENCE: 23

Gly Gly Gly Gly
1

<210> SEQ ID NO 24
<211> LENGTH: 5
<212> TYPE: PRT
<213> ORGANISM: Artificial Sequence
<220> FEATURE:
<223> OTHER INFORMATION: Synthetic

<400> SEQUENCE: 24

Leu Pro Glu Thr Gly
1               5

<210> SEQ ID NO 25
<211> LENGTH: 5
<212> TYPE: PRT
<213> ORGANISM: Artificial Sequence
<220> FEATURE:
<223> OTHER INFORMATION: Synthetic

<400> SEQUENCE: 25

Leu Pro Glu Thr Ala
1               5

<210> SEQ ID NO 26
<211> LENGTH: 7
<212> TYPE: PRT
<213> ORGANISM: Artificial Sequence
<220> FEATURE:
<223> OTHER INFORMATION: Synthetic
```

```
<400> SEQUENCE: 26

Thr Lys Val Asp Lys Lys Val
1               5

<210> SEQ ID NO 27
<211> LENGTH: 7
<212> TYPE: PRT
<213> ORGANISM: Artificial Sequence
<220> FEATURE:
<223> OTHER INFORMATION: Synthetic

<400> SEQUENCE: 27

Thr Lys Val Asp Lys Lys Ile
1               5

<210> SEQ ID NO 28
<211> LENGTH: 7
<212> TYPE: PRT
<213> ORGANISM: Artificial Sequence
<220> FEATURE:
<223> OTHER INFORMATION: Synthetic

<400> SEQUENCE: 28

Thr Thr Val Asp Lys Lys Leu
1               5

<210> SEQ ID NO 29
<211> LENGTH: 7
<212> TYPE: PRT
<213> ORGANISM: Artificial Sequence
<220> FEATURE:
<223> OTHER INFORMATION: Synthetic

<400> SEQUENCE: 29

Thr Glu Leu Ile Lys Arg Ile
1               5

<210> SEQ ID NO 30
<211> LENGTH: 7
<212> TYPE: PRT
<213> ORGANISM: Artificial Sequence
<220> FEATURE:
<223> OTHER INFORMATION: Synthetic

<400> SEQUENCE: 30

Thr Lys Val Asp Lys Thr Val
1               5

<210> SEQ ID NO 31
<211> LENGTH: 15
<212> TYPE: PRT
<213> ORGANISM: Artificial Sequence
<220> FEATURE:
<223> OTHER INFORMATION: Synthetic

<400> SEQUENCE: 31

Glu Pro Lys Ser Cys Asp Lys Thr His Thr Cys Pro Pro Cys Pro
1               5                   10                  15

<210> SEQ ID NO 32
<211> LENGTH: 12
<212> TYPE: PRT
<213> ORGANISM: Artificial Sequence
<220> FEATURE:
<223> OTHER INFORMATION: Synthetic
```

```
<400> SEQUENCE: 32

Glu Arg Lys Cys Cys Val Glu Cys Pro Pro Cys Pro
1               5                   10

<210> SEQ ID NO 33
<211> LENGTH: 12
<212> TYPE: PRT
<213> ORGANISM: Artificial Sequence
<220> FEATURE:
<223> OTHER INFORMATION: Synthetic

<400> SEQUENCE: 33

Glu Ser Lys Tyr Gly Pro Pro Cys Pro Ser Cys Pro
1               5                   10

<210> SEQ ID NO 34
<211> LENGTH: 16
<212> TYPE: PRT
<213> ORGANISM: Artificial Sequence
<220> FEATURE:
<223> OTHER INFORMATION: Synthetic

<400> SEQUENCE: 34

Glu Pro Arg Gly Pro Thr Ile Lys Pro Cys Pro Pro Cys Lys Cys Pro
1               5                   10                  15

<210> SEQ ID NO 35
<211> LENGTH: 20
<212> TYPE: PRT
<213> ORGANISM: Artificial Sequence
<220> FEATURE:
<223> OTHER INFORMATION: Synthetic

<400> SEQUENCE: 35

Glu Pro Arg Gly Pro Thr Gln Asn Pro Cys Pro Pro Leu Lys Glu Cys
1               5                   10                  15

Pro Pro Cys Ala
            20

<210> SEQ ID NO 36
<211> LENGTH: 22
<212> TYPE: PRT
<213> ORGANISM: Artificial Sequence
<220> FEATURE:
<223> OTHER INFORMATION: Synthetic

<400> SEQUENCE: 36

Glu Pro Ser Gly Pro Ile Ser Thr Ile Asn Pro Cys Pro Pro Cys Lys
1               5                   10                  15

Glu Cys His Lys Cys Pro
            20

<210> SEQ ID NO 37
<211> LENGTH: 16
<212> TYPE: PRT
<213> ORGANISM: Artificial Sequence
<220> FEATURE:
<223> OTHER INFORMATION: Synthetic

<400> SEQUENCE: 37

Glu Pro Arg Ile Pro Lys Pro Ser Thr Pro Pro Gly Ser Ser Cys Pro
1               5                   10                  15
```

```
<210> SEQ ID NO 38
<211> LENGTH: 11
<212> TYPE: PRT
<213> ORGANISM: Artificial Sequence
<220> FEATURE:
<223> OTHER INFORMATION: Synthetic

<400> SEQUENCE: 38

Ala Pro Ser Thr Cys Ser Lys Pro Thr Cys Pro
1               5                   10

<210> SEQ ID NO 39
<211> LENGTH: 14
<212> TYPE: PRT
<213> ORGANISM: Artificial Sequence
<220> FEATURE:
<223> OTHER INFORMATION: Synthetic

<400> SEQUENCE: 39

Glu Pro Gly Cys Pro Asp Pro Cys Lys His Cys Arg Cys Pro
1               5                   10

<210> SEQ ID NO 40
<211> LENGTH: 12
<212> TYPE: PRT
<213> ORGANISM: Artificial Sequence
<220> FEATURE:
<223> OTHER INFORMATION: Synthetic

<400> SEQUENCE: 40

Ala Pro Pro Val Ala Gly Pro Ser Val Phe Leu Phe
1               5                   10

<210> SEQ ID NO 41
<211> LENGTH: 13
<212> TYPE: PRT
<213> ORGANISM: Artificial Sequence
<220> FEATURE:
<223> OTHER INFORMATION: Synthetic

<400> SEQUENCE: 41

Ala Pro Glu Phe Leu Gly Gly Pro Ser Val Phe Leu Phe
1               5                   10

<210> SEQ ID NO 42
<211> LENGTH: 10
<212> TYPE: PRT
<213> ORGANISM: Artificial Sequence
<220> FEATURE:
<223> OTHER INFORMATION: Synthetic

<400> SEQUENCE: 42

Val Pro Glu Val Ser Ser Val Phe Ile Phe
1               5                   10

<210> SEQ ID NO 43
<211> LENGTH: 13
<212> TYPE: PRT
<213> ORGANISM: Artificial Sequence
<220> FEATURE:
<223> OTHER INFORMATION: Synthetic

<400> SEQUENCE: 43

Ala Pro Asn Leu Leu Gly Gly Pro Ser Val Phe Ile Phe
1               5                   10
```

<210> SEQ ID NO 44
<211> LENGTH: 13
<212> TYPE: PRT
<213> ORGANISM: Artificial Sequence
<220> FEATURE:
<223> OTHER INFORMATION: Synthetic

<400> SEQUENCE: 44

Ala Pro Asp Leu Leu Gly Gly Pro Ser Val Phe Ile Phe
1               5                   10

<210> SEQ ID NO 45
<211> LENGTH: 13
<212> TYPE: PRT
<213> ORGANISM: Artificial Sequence
<220> FEATURE:
<223> OTHER INFORMATION: Synthetic

<400> SEQUENCE: 45

Ala Pro Asn Leu Glu Gly Gly Pro Ser Val Phe Ile Phe
1               5                   10

<210> SEQ ID NO 46
<211> LENGTH: 13
<212> TYPE: PRT
<213> ORGANISM: Artificial Sequence
<220> FEATURE:
<223> OTHER INFORMATION: Synthetic

<400> SEQUENCE: 46

Ala Pro Asn Leu Glu Gly Gly Pro Ser Val Phe Ile Phe
1               5                   10

<210> SEQ ID NO 47
<211> LENGTH: 13
<212> TYPE: PRT
<213> ORGANISM: Artificial Sequence
<220> FEATURE:
<223> OTHER INFORMATION: Synthetic

<400> SEQUENCE: 47

Pro Pro Glu Leu Leu Gly Gly Pro Ser Val Phe Ile Phe
1               5                   10

<210> SEQ ID NO 48
<211> LENGTH: 13
<212> TYPE: PRT
<213> ORGANISM: Artificial Sequence
<220> FEATURE:
<223> OTHER INFORMATION: Synthetic

<400> SEQUENCE: 48

Pro Pro Glu Leu Pro Gly Gly Pro Ser Val Phe Ile Phe
1               5                   10

<210> SEQ ID NO 49
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa can be any naturally occurring amino acid

```
<400> SEQUENCE: 49

Leu Pro Xaa Thr Gly Gly Gly
1               5
```